US010100284B2

(12) United States Patent
Tanaka et al.

(10) Patent No.: US 10,100,284 B2
(45) Date of Patent: Oct. 16, 2018

(54) METHOD FOR INDUCING DIFFERENTIATION OF PLURIPOTENT STEM CELLS INTO ENDODERMAL CELLS

(71) Applicant: TOAGOSEI CO., LTD., Tokyo (JP)

(72) Inventors: Kenichi Tanaka, Ryugasaki (JP); Tetsuhiko Yoshida, Tsukuba (JP); Nahoko Baileykobayashi, Tsukuba (JP)

(73) Assignee: TOAGOSEI CO. LTD., Tokyo (JP)

( * ) Notice: Subject to any disclaimer, the term of this patent is extended or adjusted under 35 U.S.C. 154(b) by 0 days.

(21) Appl. No.: 15/107,726

(22) PCT Filed: Dec. 24, 2014

(86) PCT No.: PCT/JP2014/084144
§ 371 (c)(1),
(2) Date: Jun. 23, 2016

(87) PCT Pub. No.: WO2015/098962
PCT Pub. Date: Jul. 2, 2015

(65) Prior Publication Data
US 2016/0326488 A1 Nov. 10, 2016

(30) Foreign Application Priority Data
Dec. 25, 2013 (JP) .................. 2013-268071

(51) Int. Cl.
*C12N 5/071* (2010.01)
*C07K 14/47* (2006.01)

(52) U.S. Cl.
CPC .......... *C12N 5/067* (2013.01); *C07K 14/4711* (2013.01); *C07K 2319/10* (2013.01); *C12N 2501/998* (2013.01); *C12N 2506/45* (2013.01)

(58) Field of Classification Search
None
See application file for complete search history.

(56) References Cited

U.S. PATENT DOCUMENTS

| 2009/0068742 A1 | 3/2009 | Yamanaka |
| 2009/0325288 A1 | 12/2009 | Koshimizu et al. |
| 2010/0297758 A1 | 11/2010 | Yoshida et al. |
| 2012/0035112 A1 | 2/2012 | Yoshida et al. |
| 2012/0052576 A1* | 3/2012 | Rezania ............... C12N 5/0678 435/377 |
| 2013/0005034 A1 | 1/2013 | Yoshida et al. |
| 2014/0051171 A1 | 2/2014 | Christensen et al. |
| 2015/0126434 A1 | 5/2015 | Kobayashi et al. |

FOREIGN PATENT DOCUMENTS

| EP | 2263705 A1 | 12/2010 |
| JP | 2009165481 A | 7/2009 |
| JP | 2009215191 A | 9/2009 |
| JP | 2013-535973 A | 9/2013 |
| WO | WO 2005040391 A1 * | 5/2005 ............. C12N 15/85 |
| WO | 2007126077 A1 | 11/2007 |
| WO | 2009093692 A1 | 7/2009 |
| WO | 2010/117079 A1 | 10/2010 |
| WO | 2013/062140 A1 | 5/2013 |
| WO | 2013/180011 A1 | 12/2013 |
| WO | 2016/175303 A1 | 11/2016 |

OTHER PUBLICATIONS

Calbiochem.TPB. Datasheet [online]. Copyright 2017. EMD Millipore Corporation [retrieved on Sep. 9, 2017]. Retrieved from the Internet: <URL: http(s)://www.emdmillipore.com/US/en/product/a-Amyloid-Precursor-Protein-Modulator---CAS-497259-23-1---Calbiochem,EMD_BIO-56574CI> p. 1.*
Sprecher, C.A. et al. 1993. Molecular cloning of the cDNA for a human amyloid precursor protein homolog: evidence for a multigene family. Biochemistry 32: 4481-4486. specif. pp. 4481, 4483.*
Eng. MT—Yoshida, T. et al. Neuronal differentiation-inducing peptide and use thereof. Intl. Patent Appl. Pub. No. WO 2010/117079 A1. specification pp. 1-24. specif. p. 19 (SEQ ID No. 21 represents instant SEQ ID No. 26).*
May 16, 2017 Search Report issued in European Patent Application No. 14873237.3.
Karim Si-Tayeb et al., "Highly efficient generation of human hepatocyte-like cells from induced pluripotent stem cells," Hepatology, Wiley, vol. 51, No. 1. Jan. 1, 2010, pp. 297-305.
Kobayashi N. et al., "A novel peptide for triggering differentiation of hepatocyte-like cells from human induced pluripotent stem cells," FEBS Journal, [Online] vol. 281, Suppl. No. 1, SUN-449, Sep. 30, 2014.
Song, Zhihua et al, "Efficient generation of hepatocyte-like cells from human induced pluripotent stem cells", Cell Research, 2009, vol. 19, pp. 1233-1242.
Shiraki, Nobuaki et al, "Efficient Differentiation of Embryonic Stem Cells into Hepatic Cells In Vitro Using a Feeder-Free Basement Membrane Substratum", Aug. 2011, Plos One, vol. 6, No. 8, e24228, pp. 1-10.

(Continued)

*Primary Examiner* — Renee Claytor
*Assistant Examiner* — Sharon M. Papciak
(74) *Attorney, Agent, or Firm* — Oliff PLC

(57) ABSTRACT

A synthetic peptide having a stem cell differentiation-inducing activity to induce differentiation of pluripotent stem cells into endodermal cells, a stem cell differentiation inducer having this peptide as an active ingredient, and a method for inducing differentiation of pluripotent stem cells using these. The synthetic peptide provided by the present invention contains a stem cell differentiation-inducing peptide sequence, and this stem cell differentiation-inducing peptide sequence is selected from (1) an amino acid sequence constituting a signal peptide in any of amyloid precursor proteins (APP), amyloid precursor-like protein (APLP) 1 and APLP2, which are known as proteins belonging to the APP family, (2) a partial amino acid sequence constituting the signal peptide, or (3) a modified amino acid sequence formed by substitution, deletion and/or addition of 1, 2 or 3 amino acid residues in these amino acid sequences.

8 Claims, 5 Drawing Sheets
Specification includes a Sequence Listing.

(56) References Cited

OTHER PUBLICATIONS

Mar. 31, 2015 Search Report issued in International Patent Application No. PCT/JP2014/084144.
Mar. 31, 2015 Written Opinion issued in International Patent Application No. PCT/JP2014/084144.
Shariati S. Ali M. "APLP2 regulates neuronal stem cell differentiation during cortical development". Journal of Cell Science, vol. 126, p. 1268-1277, Mar. 2013.
Freude, Kristine K. "Soluble Amyloid Precursor Protien Induces Rapid Neural Differentiation of Human embryonic stem cells". J. Biol. Chem., vol. 286, No. 27, p. 24264-24274, 2011.
Huang Hsiang-Po, "Factors from Human Embryonic Stem Cell-derived Fibroblast-like Cells Promote topology-dependent Hepatic Differentiation in Primate Embryonic and Induced Pluripotent Stem Cells". J. Biol. Chem., vol. 285, No. 43, p. 33510-33519, 2010.
Kahoko Umeda, "ES Saibo kara Suizo Kanzo o tsukuru". Chemical Education, vol. 57, No. 10, p. 446-449, 2009.
Jan. 11, 2018 Office Action Issued in U.S. Appl. No. 15/279,890.
Patel et al., "Advances in Reprogramming Somatic Cells to Induced Pluripotent Stem Cells," Stem Cell Rev and Rep, (2010), 6:367-380.
Thomas Vierbuchen et al; "Direct conversion of fibroblasts to functional neurons by defined factors;" Nature; Feb. 25, 2010; vol. 463; pp. 1035-1041.
Zhiping P. Pang et al; "Induction of human neuronal cells by defined transcription factors;" Nature; Aug. 11, 2011; vol. 476; pp. 220-223.
Tania Aguado et al; The endocannabinoid system promotes astroglial differentiation by acting on neural progenitor cells.; The Journal of Neuroscience; Feb. 1, 2006; vol. 26; pp. 1551-1561.
U.S. Appl. No. 15/279,890, filed Sep. 29, 2016, in the name of Nahoko Baileykobayashi.

\* cited by examiner

SEQUENCE LISTING

```
<160> NUMBER OF SEQ ID NOS: 34

<210> SEQ ID NO 1
<211> LENGTH: 29
<212> TYPE: PRT
<213> ORGANISM: Artificial sequence
<220> FEATURE:
<223> OTHER INFORMATION: Synthetic peptide

<400> SEQUENCE: 1

Met Ala Ala Thr Gly Thr Ala Ala Ala Ala Ala Thr Gly Arg Leu Leu
1               5                   10                  15

Leu Leu Leu Leu Val Gly Leu Thr Ala Pro Ala Leu Ala
                20                  25

<210> SEQ ID NO 2
<211> LENGTH: 29
```

```
<212> TYPE: PRT
<213> ORGANISM: Artificial sequence
<220> FEATURE:
<223> OTHER INFORMATION: Synthetic peptide

<400> SEQUENCE: 2

Met Ala Ala Thr Gly Thr Ala Ala Ala Ala Thr Gly Lys Leu Leu
1               5                   10                  15

Val Leu Leu Leu Leu Gly Leu Thr Ala Pro Ala Ala Ala
            20                  25

<210> SEQ ID NO 3
<211> LENGTH: 38
<212> TYPE: PRT
<213> ORGANISM: Artificial sequence
<220> FEATURE:
<223> OTHER INFORMATION: Synthetic peptide

<400> SEQUENCE: 3

Met Gly Pro Ala Ser Pro Ala Ala Arg Gly Leu Ser Arg Arg Pro Gly
1               5                   10                  15

Gln Pro Pro Leu Pro Leu Leu Leu Pro Leu Leu Leu Leu Leu Leu Arg
            20                  25                  30

Ala Gln Pro Ala Ile Gly
        35

<210> SEQ ID NO 4
<211> LENGTH: 37
<212> TYPE: PRT
<213> ORGANISM: Artificial sequence
<220> FEATURE:
<223> OTHER INFORMATION: Synthetic peptide

<400> SEQUENCE: 4

Met Gly Pro Thr Ser Pro Ala Ala Arg Gly Gln Gly Arg Arg Trp Arg
1               5                   10                  15

Pro Pro Leu Pro Leu Leu Leu Pro Leu Ser Leu Leu Leu Leu Arg Ala
            20                  25                  30

Gln Leu Ala Val Gly
        35

<210> SEQ ID NO 5
<211> LENGTH: 17
<212> TYPE: PRT
<213> ORGANISM: Artificial sequence
<220> FEATURE:
<223> OTHER INFORMATION: Synthetic peptide

<400> SEQUENCE: 5

Met Leu Pro Gly Leu Ala Leu Leu Leu Leu Ala Ala Trp Thr Ala Arg
1               5                   10                  15

Ala

<210> SEQ ID NO 6
<211> LENGTH: 17
<212> TYPE: PRT
<213> ORGANISM: Artificial sequence
<220> FEATURE:
<223> OTHER INFORMATION: Synthetic peptide

<400> SEQUENCE: 6

Met Leu Pro Ser Leu Ala Leu Leu Leu Leu Ala Ala Trp Thr Val Arg
1               5                   10                  15
```

Ala

```
<210> SEQ ID NO 7
<211> LENGTH: 13
<212> TYPE: PRT
<213> ORGANISM: Artificial sequence
<220> FEATURE:
<223> OTHER INFORMATION: synthetic peptide

<400> SEQUENCE: 7

Lys Lys Arg Thr Leu Arg Lys Asn Asp Arg Lys Lys Arg
1               5                   10

<210> SEQ ID NO 8
<211> LENGTH: 14
<212> TYPE: PRT
<213> ORGANISM: Artificial sequence
<220> FEATURE:
<223> OTHER INFORMATION: Synthetic peptide

<400> SEQUENCE: 8

Arg Ser Arg Lys Tyr Thr Ser Trp Tyr Val Ala Leu Lys Arg
1               5                   10

<210> SEQ ID NO 9
<211> LENGTH: 8
<212> TYPE: PRT
<213> ORGANISM: Artificial sequence
<220> FEATURE:
<223> OTHER INFORMATION: Synthetic peptide

<400> SEQUENCE: 9

Trp Arg Arg Gln Ala Arg Phe Lys
1               5

<210> SEQ ID NO 10
<211> LENGTH: 13
<212> TYPE: PRT
<213> ORGANISM: Artificial sequence
<220> FEATURE:
<223> OTHER INFORMATION: Synthetic peptide

<400> SEQUENCE: 10

Arg Leu Pro Val Arg Arg Arg Arg Arg Val Pro Lys
1               5                   10

<210> SEQ ID NO 11
<211> LENGTH: 11
<212> TYPE: PRT
<213> ORGANISM: Artificial sequence
<220> FEATURE:
<223> OTHER INFORMATION: Synthetic peptide

<400> SEQUENCE: 11

Tyr Gly Arg Lys Lys Arg Arg Gln Arg Arg Arg
1               5                   10

<210> SEQ ID NO 12
<211> LENGTH: 11
<212> TYPE: PRT
<213> ORGANISM: Artificial sequence
<220> FEATURE:
<223> OTHER INFORMATION: Synthetic peptide

<400> SEQUENCE: 12

Tyr Ala Arg Ala Ala Ala Arg Gln Ala Arg Ala
1               5                   10
```

<210> SEQ ID NO 13
<211> LENGTH: 16
<212> TYPE: PRT
<213> ORGANISM: Artificial sequence
<220> FEATURE:
<223> OTHER INFORMATION: Synthetic peptide

<400> SEQUENCE: 13

Arg Gln Ile Lys Ile Trp Phe Gln Asn Arg Arg Met Lys Trp Lys Lys
1               5                   10                  15

<210> SEQ ID NO 14
<211> LENGTH: 9
<212> TYPE: PRT
<213> ORGANISM: Artificial sequence
<220> FEATURE:
<223> OTHER INFORMATION: Synthetic peptide

<400> SEQUENCE: 14

Arg Arg Arg Arg Arg Arg Arg Arg Arg
1               5

<210> SEQ ID NO 15
<211> LENGTH: 19
<212> TYPE: PRT
<213> ORGANISM: Artificial sequence
<220> FEATURE:
<223> OTHER INFORMATION: Synthetic peptide

<400> SEQUENCE: 15

Gly Arg Cys Arg Arg Leu Ala Asn Phe Pro Gly Arg Lys Arg Arg
1               5                   10                  15

Arg Arg Arg

<210> SEQ ID NO 16
<211> LENGTH: 13
<212> TYPE: PRT
<213> ORGANISM: Artificial sequence
<220> FEATURE:
<223> OTHER INFORMATION: Synthetic peptide

<400> SEQUENCE: 16

Leu Leu Leu Leu Leu Leu Val Gly Leu Thr Ala Pro Ala
1               5                   10

<210> SEQ ID NO 17
<211> LENGTH: 12
<212> TYPE: PRT
<213> ORGANISM: Artificial sequence
<220> FEATURE:
<223> OTHER INFORMATION: Synthetic peptide

<400> SEQUENCE: 17

Leu Val Leu Leu Leu Leu Gly Leu Thr Ala Pro Ala
1               5                   10

<210> SEQ ID NO 18
<211> LENGTH: 13
<212> TYPE: PRT
<213> ORGANISM: Artificial sequence
<220> FEATURE:
<223> OTHER INFORMATION: Synthetic peptide

<400> SEQUENCE: 18

Pro Leu Pro Leu Leu Leu Pro Leu Leu Leu Leu Leu Leu

```
1               5                   10

<210> SEQ ID NO 19
<211> LENGTH: 13
<212> TYPE: PRT
<213> ORGANISM: Artificial sequence
<220> FEATURE:
<223> OTHER INFORMATION: Synthetic peptide

<400> SEQUENCE: 19

Leu Leu Leu Leu Leu Leu Arg Ala Gln Pro Ala Ile Gly
1               5                   10

<210> SEQ ID NO 20
<211> LENGTH: 13
<212> TYPE: PRT
<213> ORGANISM: Artificial sequence
<220> FEATURE:
<223> OTHER INFORMATION: Synthetic peptide

<400> SEQUENCE: 20

Pro Leu Pro Leu Leu Leu Pro Leu Ser Leu Leu Leu Leu
1               5                   10

<210> SEQ ID NO 21
<211> LENGTH: 13
<212> TYPE: PRT
<213> ORGANISM: Artificial sequence
<220> FEATURE:
<223> OTHER INFORMATION: Synthetic peptide

<400> SEQUENCE: 21

Leu Ser Leu Leu Leu Leu Arg Ala Gln Leu Ala Val Gly
1               5                   10

<210> SEQ ID NO 22
<211> LENGTH: 14
<212> TYPE: PRT
<213> ORGANISM: Artificial sequence
<220> FEATURE:
<223> OTHER INFORMATION: Synthetic peptide

<400> SEQUENCE: 22

Met Leu Pro Gly Leu Ala Leu Leu Leu Ala Ala Trp Thr
1               5                   10

<210> SEQ ID NO 23
<211> LENGTH: 15
<212> TYPE: PRT
<213> ORGANISM: Artificial sequence
<220> FEATURE:
<223> OTHER INFORMATION: Synthetic peptide

<400> SEQUENCE: 23

Pro Gly Leu Ala Leu Leu Leu Leu Ala Ala Trp Thr Ala Arg Ala
1               5                   10                  15

<210> SEQ ID NO 24
<211> LENGTH: 14
<212> TYPE: PRT
<213> ORGANISM: Artificial sequence
<220> FEATURE:
<223> OTHER INFORMATION: Synthetic peptide

<400> SEQUENCE: 24

Met Leu Pro Ser Leu Ala Leu Leu Leu Leu Ala Ala Trp Thr
1               5                   10
```

```
<210> SEQ ID NO 25
<211> LENGTH: 15
<212> TYPE: PRT
<213> ORGANISM: Artificial sequence
<220> FEATURE:
<223> OTHER INFORMATION: Synthetic peptide

<400> SEQUENCE: 25

Pro Ser Leu Ala Leu Leu Leu Ala Ala Trp Thr Val Arg Ala
1               5                   10                  15

<210> SEQ ID NO 26
<211> LENGTH: 27
<212> TYPE: PRT
<213> ORGANISM: Artificial sequence
<220> FEATURE:
<223> OTHER INFORMATION: Synthetic peptide

<400> SEQUENCE: 26

Leu Leu Leu Leu Leu Leu Val Gly Leu Thr Ala Pro Ala Gly Lys Lys
1               5                   10                  15

Arg Thr Leu Arg Lys Asn Asp Arg Lys Lys Arg
            20                  25

<210> SEQ ID NO 27
<211> LENGTH: 23
<212> TYPE: PRT
<213> ORGANISM: Artificial sequence
<220> FEATURE:
<223> OTHER INFORMATION: Synthetic peptide

<400> SEQUENCE: 27

Ala Ala Ala Ala Ala Thr Gly Arg Leu Leu Leu Leu Leu Val Gly
1               5                   10                  15

Leu Thr Ala Pro Ala Leu Ala
            20

<210> SEQ ID NO 28
<211> LENGTH: 16
<212> TYPE: PRT
<213> ORGANISM: Artificial sequence
<220> FEATURE:
<223> OTHER INFORMATION: Synthetic peptide

<400> SEQUENCE: 28

Arg Leu Leu Leu Leu Leu Val Gly Leu Thr Ala Pro Ala Leu Ala
1               5                   10                  15

<210> SEQ ID NO 29
<211> LENGTH: 30
<212> TYPE: PRT
<213> ORGANISM: Artificial sequence
<220> FEATURE:
<223> OTHER INFORMATION: Synthetic peptide

<400> SEQUENCE: 29

Met Leu Pro Gly Leu Ala Leu Leu Leu Ala Ala Trp Thr Ala Arg
1               5                   10                  15

Ala Lys Lys Arg Thr Leu Arg Lys Asn Asp Arg Lys Lys Arg
            20                  25                  30

<210> SEQ ID NO 30
<211> LENGTH: 36
<212> TYPE: PRT
```

<213> ORGANISM: Artificial sequence
<220> FEATURE:
<223> OTHER INFORMATION: Synthetic peptide

<400> SEQUENCE: 30

Ala Ala Ala Ala Ala Thr Gly Arg Leu Leu Leu Leu Leu Val Gly
1               5                   10                  15

Leu Thr Ala Pro Ala Leu Ala Lys Lys Arg Thr Leu Arg Lys Asn Asp
                20                  25                  30

Arg Lys Lys Arg
            35

<210> SEQ ID NO 31
<211> LENGTH: 29
<212> TYPE: PRT
<213> ORGANISM: Artificial sequence
<220> FEATURE:
<223> OTHER INFORMATION: Synthetic peptide

<400> SEQUENCE: 31

Arg Leu Leu Leu Leu Leu Val Gly Leu Thr Ala Pro Ala Leu Ala
1               5                   10                  15

Lys Lys Arg Thr Leu Arg Lys Asn Asp Arg Lys Lys Arg
                20                  25

<210> SEQ ID NO 32
<211> LENGTH: 42
<212> TYPE: PRT
<213> ORGANISM: Artificial sequence
<220> FEATURE:
<223> OTHER INFORMATION: Synthetic peptide

<400> SEQUENCE: 32

Met Ala Ala Thr Gly Thr Ala Ala Ala Ala Thr Gly Lys Leu Leu
1               5                   10                  15

Val Leu Leu Leu Leu Gly Leu Thr Ala Pro Ala Ala Lys Lys Arg
                20                  25                  30

Thr Leu Arg Lys Asn Asp Arg Lys Lys Arg
            35                  40

<210> SEQ ID NO 33
<211> LENGTH: 42
<212> TYPE: PRT
<213> ORGANISM: Artificial sequence
<220> FEATURE:
<223> OTHER INFORMATION: Synthetic peptide

<400> SEQUENCE: 33

Met Ala Ala Thr Gly Thr Ala Ala Ala Ala Thr Gly Arg Leu Leu
1               5                   10                  15

Leu Leu Leu Val Gly Leu Thr Ala Pro Ala Leu Ala Lys Lys Arg
                20                  25                  30

Thr Leu Arg Lys Asn Asp Arg Lys Lys Arg
            35                  40

<210> SEQ ID NO 34
<211> LENGTH: 51
<212> TYPE: PRT
<213> ORGANISM: Artificial sequence
<220> FEATURE:
<223> OTHER INFORMATION: Synthetic peptide

<400> SEQUENCE: 34

```
Met Gly Pro Ala Ser Pro Ala Ala Arg Gly Leu Ser Arg Arg Pro Gly
1               5                   10                  15

Gln Pro Pro Leu Pro Leu Leu Leu Pro Leu Leu Leu Leu Leu Leu Arg
            20              25                  30

Ala Gln Pro Ala Ile Gly Lys Lys Arg Thr Leu Arg Lys Asn Asp Arg
        35              40                  45

Lys Lys Arg
    50
```

METHOD FOR INDUCING DIFFERENTIATION OF PLURIPOTENT STEM CELLS INTO ENDODERMAL CELLS

TECHNICAL FIELD

The invention relates to a synthetic peptide capable of inducing differentiation or promoting induction of differentiation of pluripotent stem cells into endodermal cells, and to a use thereof. In particular, the invention relates to a stem cell differentiation inducer (composition) having this peptide as an active ingredient, and to a method for using this peptide to induce differentiation of pluripotent stem cells into endodermal cells.

The present application claims the priority right based on Japanese Patent Application No. 2013-268071, submitted on Dec. 25, 2013, and all the contents in the application are incorporated into the present description by referring to the same.

BACKGROUND ART

One issue in the field of regenerative medicine is the establishment of techniques for inducing pluripotent stem cells in an undifferentiated state, such as embryonic stem cells (ES cells) and induced pluripotent stem cells (iPS cells), to differentiate efficiently into cells having target functions (see Patent Literature 1 to 3 and Non-patent Literature 1 and 2 below).

For example, there is demand for the establishment of methods for culturing (proliferating) pluripotent stem cells in an undifferentiated state, and then inducing the increased numbers of undifferentiated pluripotent stem cells produced by this culture (proliferation) to differentiate into cells having target functions by easy and efficient methods. For example, Patent Literature 3 below describes a technique for inducing differentiation of cultured iPS cells into myocardial cells. In addition, many methods have been reported for inducing pluripotent stem cells in an undifferentiated state to differentiate into myocardial cells, blood cells, reproductive cells, nerve cells and the like.

Recently, there has been increased demand for the establishment of techniques for efficiently inducing pluripotent stem cells in an undifferentiated state to differentiate into endodermal cells (including cells constituting the endoderm, cells differentiated from the endoderm, and cells constituting endodermally-derived tissues).

Examples of endodermally-derived tissues include the liver, gallbladder, kidneys, lungs, stomach, intestines and the like. When these endodermally-derived tissues are damaged (become dysfunctional for example) by inflammation, injury, cancer, lifestyle-related disease or the like, the patient's quality of life (QOL) is often severely impacted. Therefore, there is demand for the establishment of regenerative medicine therapies as one means of effectively treating such dysfunction of endodermally-derived tissues. For example, there is demand for the establishment of techniques for culturing (proliferating) pluripotent stem cells in an undifferentiated state, inducing the increased numbers of undifferentiated pluripotent stem cells produced by this culture (proliferation) to differentiate into endodermal cells by easy and efficient methods, and then supplying the endodermal cells obtained by such differentiation induction to regenerative medicine.

Of the endodermal cells, particular attention has focused on techniques for efficiently inducing differentiation into hepatocytes. The liver serves a very large number of functions in the living body, including metabolism, detoxification, drug metabolism, excretion, and fluid homeostasis. Moreover, the liver is sometimes called the "silent organ" because liver tissue may produce few subjective symptoms, so that damage (dysfunction) is often fairly advanced when treatment is initiated. Liver transplantation (including hepatocyte transplantation) is effective, but conventional transplantation therapy suffers from problems of donor shortage and organ rejection. Thus, hepatocytes and liver precursor cells capable of being used in regenerative medicine would be useful for the establishment therapies to treat liver damage (disease, dysfunction).

The establishment of techniques for efficiently inducing differentiation of pluripotent stem cells into endodermal cells is also anticipated in a variety of fields apart from regenerative medicine, including fundamental medicine, drug discovery, pharmacology and embryology. For example, endodermal cells that have been induced to differentiate from pluripotent stem cells can be used to conduct in vitro research on pathogenesis and drug development for diseases which have been difficult to study in detail in the past. In particular, techniques of inducing differentiation of hepatocytes from pluripotent stem cells hold promise as a means of resolving the problem of stably supplying uniform cells, which is a problem in toxicity evaluation performed using human primary culture hepatocytes in the process of drug development research. Moreover, techniques of inducing differentiation of pancreatic cells from pluripotent stem cells are of interest from the standpoint of supplying insulin that can be used in diabetes treatment.

However, the methods that have been reported for inducing differentiation of pluripotent stem cells into endodermal cells often involve complex operations (for example, differentiation induction methods involving introduction of multiple exogenous genes) or if the operations are relatively easy (addition of multiple kinds of differentiation-inducing compounds in liquid form to medium for example), differentiation efficiency is low. Moreover, differentiation induction methods involving introduction of exogenous genes present safety issues because the exogenous genes are incorporated into genome DNA, while differentiation induction by addition of differentiation-inducing compounds presents cost issues because large quantities of expensive cytokines and other liquid factors are required. Even when it is possible to induce differentiation of pluripotent stem cells into endodermal cells, moreover, the resulting cells often do not function satisfactorily. There is thus demand for methods of inducing differentiation more easily and with greater differentiation efficiency.

CITATION LIST

Patent Literature

[Patent Literature 1] Japanese Patent Application Publication No. 2009-165481
[Patent Literature 2] Japanese Patent Application Publication No. 2009-215191
[Patent Literature 3] WO 2007/126077
[Patent Literature 4] WO 2009/093692

Non Patent Literature

[Non-patent Literature 1] Cell Research, Vol. 19, 2009, pp. 1233-1242

[Non-patent Literature 2] PLOS ONE, Vol. 6 (No. 8), 2011, e24228

SUMMARY OF INVENTION

It is an object of the present invention to provide an artificially synthesizable peptide with a relatively short chain length, which is a synthetic peptide that contributes to the object of inducing differentiation or promoting (aiding) induction of differentiation of pluripotent stem cells into endodermal cells by a method different from conventional differentiation induction methods. Another object is to provide a stem cell differentiation inducer (pharmaceutical composition) having this peptide as an active ingredient. Another object is to provide a method for using such a peptide to induce differentiation or promote (aid) induction of differentiation of pluripotent stem cells into endodermal cells.

After exhaustive research into a variety of peptides with the aim of contributing to the object of inducing differentiation of pluripotent stem cells into endodermal cells, the inventors discovered that, surprisingly, synthetic peptides containing all or part of amino acid sequences (including modified amino acid sequences), which are amino acid sequences (hereinafter sometimes referred to as signal peptide sequences) constituting signal peptides of amyloid precursor protein (APP), a protein known for functions entirely unrelated to induction of cell differentiation, and two amyloid precursor-like proteins (Amyloid Precursor-Like Protein 1: APLP1, Amyloid Precursor-Like Protein 2: APLP2), which are proteins related to APP, have stem cell differentiation-inducing abilities (stem cell differentiation-inducing activity) for inducing at least one kind of pluripotent stem cell to differentiate into endodermal cells, thereby perfecting the present invention.

The stem cell differentiation inducer provided by the present invention is a differentiation inducer for inducing differentiation of pluripotent stem cells into endodermal cells, the inducer containing as an active ingredient a synthetic peptide containing a stem cell differentiation-inducing peptide sequence that induces differentiation of pluripotent stem cells into endodermal cells, wherein the stem cell differentiation-inducing peptide sequence is selected from among:

an amino acid sequence constituting a signal peptide of any protein belonging to an amyloid precursor protein (APP) family (typically, any of APP, APLP1 and APLP2);

a partial amino acid sequence having continuous amino acid residues of a part of an amino acid sequence constituting this signal peptide; and a modified amino acid sequence formed by substitution, deletion and/or addition of 1, 2 or 3 amino acid residues in these amino acid sequences.

Typically, this stem cell differentiation inducer (pharmaceutical composition) contains at least one kind of pharmaceutically acceptable carrier (for example, at least one kind of base material contributing to greater stability of the peptide, or a liquid medium such as physiological saline or various buffers or the like).

In this Description, a synthetic peptide containing a stem cell differentiation-inducing peptide sequence (that is, a synthetic peptide having stem cell differentiation-inducing activity) is also called a "differentiation-inducing synthetic peptide".

Moreover, in this Description an amino acid sequence constituting a signal peptide of amyloid precursor protein (APP) or two amyloid precursor-like proteins (APLP1, APLP2), or a partial amino acid sequence of such a signal peptide sequence (that is, the continuous partial sequence of a part of these) may also be called an "APP signal peptide-associated sequence".

Because the stem cell differentiation inducer disclosed here contains a differentiation-inducing synthetic peptide with a simple structure (typically, a straight peptide chain) as an active ingredient, target pluripotent stem cells can be induced to differentiate into endodermal stem cells by the simple process of supplying the stem cell differentiation inducer to the target pluripotent stem cells (typically, a medium in which such cells are cultured). Because it has as an active ingredient a synthetic peptide that is easy to manufacture artificially by chemical synthesis (or biosynthesis), moreover, the stem cell differentiation inducer can be prepared easily and at low cost in the desired quantity. Because the stem cell differentiation inducer disclosed here can induce pluripotent stem cells to differentiate into endodermal cells without the use of large quantities of expensive cytokines and other liquid factors (typically, as a liquid factor substitute), the costs involved in inducing differentiation of pluripotent stem cells into endodermal stem cells can be reduced. Moreover, no exogenous genes are incorporated into genome DNA because no exogenous genes are introduced.

In a preferred embodiment of the stem cell differentiation inducer disclosed here, the stem cell differentiation-inducing peptide sequence contained in the differentiation-inducing synthetic peptide is selected from the amino acid sequences of i) through iv) below.

i) Amino acid sequence of SEQ ID NO:1:

```
                                          (SEQ ID NO: 1)
       MAATGTAAAAATGRLLLLLLVGLTAPALA;
``` or a part of the amino acid sequence represented by SEQ ID NO:1 that is a partial amino acid sequence having at least 13 continuous amino acid residues from the #15 leucine residue to the #27 alanine residue counting from the N-terminal amino acid residue of that amino acid sequence; or a modified amino acid sequence formed by substitution, deletion or addition of 1, 2 or 3 amino acid residues in these amino acid sequences.

ii) Amino acid sequence of SEQ ID NO:2:

```
                                          (SEQ ID NO: 2)
       MAATGTAAAAATGKLLVLLLLGLTAPAAA;
``` or a part of the amino acid sequence represented by SEQ ID NO:2 that is a partial amino acid sequence having at least 12 continuous amino acid residues from the #16 leucine residue to the #27 alanine residue counting from the N-terminal amino acid residue of that amino acid sequence; or a modified amino acid sequence formed by substitution, deletion or addition of 1, 2 or 3 amino acid residues in these amino acid sequences.

iii) Amino acid sequence of SEQ ID NO:3:

```
                                          (SEQ ID NO: 3)
     MGPASPAARGLSRRPGQPPLPLLLPLLLLLLRAQPAIG;
``` or a part of the amino acid sequence represented by SEQ ID NO:3 that is a partial amino acid sequence having at least 13 continuous amino acid residues from the #19 proline residue to the #31 leucine residue counting from the N-terminal amino acid residue of that amino acid sequence; or a part of the amino acid sequence represented by SEQ ID NO:3 that is a partial amino acid sequence having at least 13 continuous amino acid residues from the #26 leucine residue to the #38 glycine residue counting from the N-terminal amino acid residue of that amino acid sequence; or a modified amino acid sequence formed by substitution, deletion or addition of 1, 2 or 3 amino acid residues in these amino acid sequences.

iv) Amino acid sequence of SEQ ID NO:4:

```
                                            (SEQ ID NO: 4)
MGPTSPAARGQGRRWRPPLPLLLPLSLLLLRAQLAVG;
``` or a part of the amino acid sequence represented by SEQ ID NO:4 that is a partial amino acid sequence having at least 13 continuous amino acid residues from the #18 proline residue to the #30 leucine residue counting from the N-terminal amino acid residue of that amino acid sequence; or a part of the amino acid sequence represented by SEQ ID NO:4 that is a partial amino acid sequence having at least 13 continuous amino acid residues from the #25 leucine residue to the #37 glycine residue counting from the N-terminal amino acid residue of that amino acid sequence; or a modified amino acid sequence formed by substitution, deletion or addition of 1, 2 or 3 amino acid residues in these amino acid sequences.

v) Amino acid sequence of SEQ ID NO:5:

```
                            (SEQ ID NO: 5)
MLPGLALLLLAAWTARA;
``` or a part of the amino acid sequence represented by SEQ ID NO:5 that is a partial amino acid sequence having at least 14 continuous amino acid residues from the #1 methionine residue to the #14 threonine residue counting from the N-terminal amino acid residue of that amino acid sequence; or a part of the amino acid sequence represented by SEQ ID NO:5 that is a partial amino acid sequence having at least 15 continuous amino acid residues from the #3 proline residue to the #17 alanine residue counting from the N-terminal amino acid residue of that amino acid sequence; or a modified amino acid sequence formed by substitution, deletion or addition of 1, 2 or 3 amino acid residues in these amino acid sequences.

vi) Amino acid sequence of SEQ ID NO:6:

```
                            (SEQ ID NO: 6)
MLPSLALLLLAAWTVRA;
``` or a part of the amino acid sequence represented by SEQ ID NO:6 that is a partial amino acid sequence having at least 14 continuous amino acid residues from the #1 methionine residue to the #14 threonine residue counting from the N-terminal amino acid residue of that amino acid sequence; or a part of the amino acid sequence represented by SEQ ID NO:6 that is a partial amino acid sequence having at least 15 continuous amino acid residues from the #3 proline residue to the #17 alanine residue counting from the N-terminal amino acid residue of that amino acid sequence; or a modified amino acid sequence formed by substitution, deletion or addition of 1, 2 or 3 amino acid residues in these amino acid sequences.

The amino acid sequences represented by SEQ ID NOS:1 to 6 are typical examples of amino acid sequence constituting signal peptides of proteins in the APP family. Moreover, the amino acid sequences represented by SEQ ID NOS:1 to 6 and the partial amino acid sequences of these amino acid sequences disclosed here are typical examples of APP signal peptide-associated sequences. These amino acid sequences or modified amino acid sequences of these may be adopted favorably for carrying out the present invention.

Preferably, the differentiation-inducing synthetic peptide contained in the stem cell differentiation inducer has a transmembrane peptide sequence on the N-terminal side or the C-terminal side of the amino acid sequence of the stem cell differentiation-inducing peptide sequence.

The stem cell differentiation-inducing peptide sequence can be efficiently transported from the outside (outside the cell membrane) to the inside of pluripotent stem cells by adding a differentiation-inducing synthetic peptide containing such a transmembrane peptide sequence to target pluripotent stem cells (typically in medium).

Preferably, the differentiation-inducing synthetic peptide contained in the stem cell differentiation inducer has the following amino acid sequence as the transmembrane peptide sequence:

```
                            (SEQ ID NO: 7)
KKRTLRKNDRKKR.
```

The amino acid sequence disclosed here as SEQ ID NO:7 is a typical example of an amino acid sequence constituting a transmembrane peptide, and can be used favorably in carrying out the present invention.

In a preferred embodiment of the differentiation-inducing synthetic peptide contained in the stem cell differentiation inducer disclosed here, the total number of amino acid residues constituting the peptide is 100 or less. A peptide with such a short peptide chain is preferred as a component of the stem cell differentiation inducer because it is easy to chemically synthesize, as well as being inexpensive and easy to handle.

Preferably, the differentiation-inducing synthetic peptide contained in the stem cell differentiation inducer has any of the following amino acid sequences:

```
                            (SEQ ID NO: 26)
LLLLLLVGLTAPAGKKRTLRKNDRKKR (SEQ ID NO: 29)
MLPGLALLLLAAWTARAKKRTLRKNDRKKR (SEQ ID NO: 30)
AAAAATGRLLLLLLVGLTAPALAKKRTLRKNDRKKR (SEQ ID NO: 31)
RLLLLLLVGLTAPALAKKRTLRKNDRKKR (SEQ ID NO: 32)
MAATGTAAAAATGKLLVLLLLGLTAPAAAKKRTLRKNDRKKR (SEQ ID NO: 33)
MAATGTAAAAATGRLLLLLLVGLTAPALAKKRTLRKNDRKKR (SEQ ID NO: 34)
MGPASPAARGLSRRPGQPPLPLLLPLLLLLLRAQPAIGKKRT
LRKNDRKKR.
```

A stem cell differentiation inducer containing such a differentiation-inducing synthetic peptide is desirable for use in inducing pluripotent stem cells derived from humans in particular or mammals other than humans (such as iPS) cells to differentiate into endodermal cells.

Preferably, the stem cell differentiation inducer disclosed here is used with iPS cells derived from humans or mammals other than humans. In the field of regenerative medicine, it is especially desirable to induce differentiation into endodermal cells of iPS cells, which are easier to obtain than ES cells.

Preferably, the stem cell differentiation inducer disclosed here causes increased expression, in the pluripotent stem cells, of Alpha-Fetoprotein (AFP) or albumin protein (ALB), which is protein that is known as a marker of differentiation into endodermal cells. Increased expression of AFP or ALB can be seen as an indicator that pluripotent stem cells have been induced to differentiate into endodermal cells (typically, liver precursor cells or hepatocytes).

Preferably, with the stem cell differentiation inducer disclosed here, the endodermal cells are at least one of liver precursor cells and hepatocytes. Such a stem cell differentiation inducer is extremely valuable in the field of regenerative medicine for liver disease in particular.

The present invention also provides a method for inducing at least one kind of pluripotent stem cells (typically, pluripotent stem cells cultured in vitro) to differentiate into endodermal cells in vitro, the method including: culturing target pluripotent stem cells; and supplying at least once any of the stem cell differentiation inducers disclosed here (or in other words any of the differentiation-inducing synthetic peptides disclosed here) to the pluripotent stem cells in the culture.

With this differentiation induction method, as discussed above, the costs involved in inducing differentiation of pluripotent stem cells into endodermal cells can be reduced or cost increases can be controlled because the use of expensive liquid factors can be eliminated or reduced. Moreover, differentiation of pluripotent stem cells into endodermal cells can be achieved with great efficiency by a simple process of supplying the stem cell differentiation inducer (differentiation-inducing synthetic peptide) to the target pluripotent stem cells (typically, to a medium containing the cells).

The differentiation induction method disclosed here can be implemented favorably as a method for inducing differentiation into endodermal cells of iPS cells derived from humans or non-human mammals. Human-derived iPS cells are especially desirable. This method for inducing differentiation of human-derived iPS cells into endodermal cells is extremely valuable in the medical industry.

Preferably, the differentiation induction method disclosed here increased expression in the pluripotent stem cells of AFP or ALB, which are proteins that are known as markers of differentiation into endodermal cells. Pluripotent stem cells can be induced to differentiate into endodermal cells by increasing expression of AFP or ALB.

Another aspect of the present invention provides a method for producing a culture containing hepatocytes and/or liver precursor cells from a culture containing pluripotent stem cells, wherein the stem cell differentiation inducer disclosed here is supplied at least once in a culture containing the pluripotent stem cells in the process of inducing differentiation of pluripotent stem cells into hepatocytes in a culture containing pluripotent stem cells.

With this production method, hepatocytes and/or liver precursor cells can be produced efficiently from pluripotent stem cells by simple, inexpensive methods.

The stem cell differentiation-inducing method disclosed here can also be implemented favorably with the aim of promoting repair or regeneration of an affected part in a test subject (patient). That is, because cells useful for repair or regeneration can be efficiently induced to differentiate (produced) in vitro by the method disclosed here, the time required for repair or regeneration can be shortened by introducing cells that have been efficiently induced to differentiate in vitro by this method into the body of a test subject (patient). Moreover, the problems of donor shortage and rejection are resolved because the method uses pluripotent stem cells obtained from the test subject (patient).

The stem cell differentiation-inducing method disclosed here can also be implemented favorably with the aim of producing a tissue or organ that can be transplanted into a test subject (patient). That is, because the method disclosed here is a method for efficiently inducing differentiation of (producing) endodermal cells having the ability to differentiate into endodermal tissue, endodermal cells that have been induced to differentiate efficiently in vitro by the method of the invention can be further proliferated and grown into a target tissue body (liver, gallbladder, kidney, lung, stomach, intestine or the like or a part of such a tissue body) to efficiently produce such a tissue body.

DESCRIPTION OF EMBODIMENTS

Figure 1:
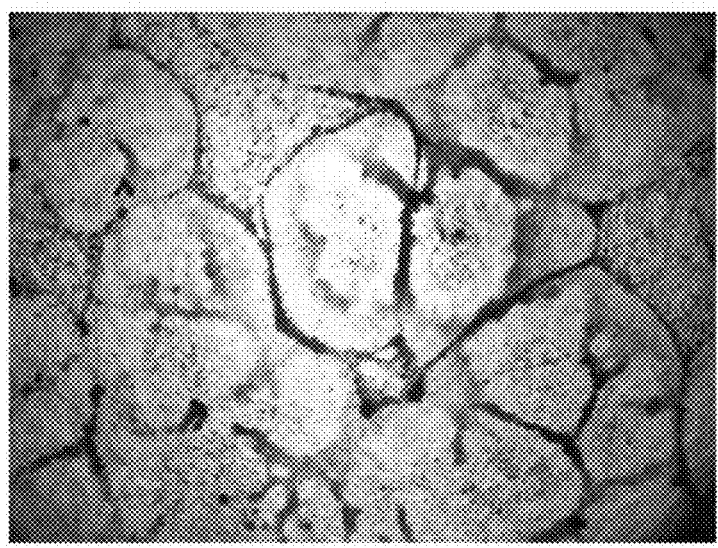
FIG. 1 is an optical microscope image showing structural changes in iPS cells cultured after addition of a differentiation-inducing synthetic peptide of one embodiment.

Preferred embodiments of the invention are explained below. Matters other than those explicitly mentioned in this Description (such as the primary structure and chain length of the synthetic peptide disclosed here) that are necessary for implementing the invention (for example, chemical synthesis of peptides, cell culture techniques, and ordinary matters related to preparation of drug compositions having the peptide as an ingredient) can be understood as designed matters by a person skilled in the art based on conventional technology in the fields of cell engineering, physiology, medicine, pharmacology, organic chemistry, biochemistry, genetic engineering, protein engineering, molecular biology, genetics and the like. The invention can be implemented based on the content disclosed in this Description and on technical common knowledge in these fields. In the explanations below, amino acids are sometimes expressed with 1-letter abbreviations based on the nomenclature for amino acids given in the IUPAC-IUB guidelines (but 3-letter abbreviations are used in the sequence tables).

The entire content of all literature cited in this Description is incorporated by reference into this Description.

In this Description, a "synthetic peptide" is not a peptide chain that can exist stably in nature by itself, but is a peptide fragment that has been artificially manufactured by chemical synthesis or biosynthesis (that is, produced based on bioengineering), and can exist stably in a specific composition (for example, a stem cell differentiation inducer capable of inducing differentiation of pluripotent stem cells into endodermal cells).

Moreover, in this Description the term "peptide" refers to an amino acid polymer having multiple peptide bonds, and while the number of amino acid residues in the peptide chain is not particularly limited, typically the molecular weight is relatively low, with a total number of amino acid residues of 100 or fewer (preferably 60 or fewer, such as 50 or fewer).

Except when otherwise specified, the term "amino acid residue" in this description encompasses the N-terminal amino acid and C-terminal amino acid of the peptide chain.

In the amino acid sequences described in this Description, the left side is normally the N-terminal side and the right side is the C-terminal side.

In this Description, a "modified amino acid sequence" is an amino acid sequence formed by substitution, deletion and/or addition (insertion) of 1 or more (such as 2 or 3) amino acid residues in a specific amino acid sequence without sacrificing the function of that specific amino acid sequence (such as the stem cell differentiation-inducing ability of a differentiation-inducing synthetic peptide, or the ability of a transmembrane peptide to move from outside to inside the cell). Typical examples of modified amino acid sequences in this description include sequences produced by so-called conservative amino acid replacement of 1 or more (typically 2 or 3) amino acid residues (for example, sequences having basic amino acid residues replaced with other basic amino acid residues, such as by mutual substitution of a lysine residue and an arginine residue), and sequences comprising one or more (typically 2 or 3) amino acid residues added (inserted) or deleted in a specific amino acid sequence. Thus, the differentiation-inducing synthetic peptide disclosed here encompasses not only synthetic peptides composed of amino acid sequences identical to the amino acid sequences of the sequence ID numbers, but also synthetic peptides consisting of amino acid sequences comprising the amino acid sequences of the sequence ID numbers with 1 or more (typically 2 or 3) amino acid residues substituted (by conservative substitution for example), deleted and or added, and exhibiting similar stem cell differentiation-inducing properties.

In this Description, a "stem cell" is a cell having self-replicating ability and the ability to differentiate into one or more or preferably two or more kinds of cells, tissues or organs. In this Description, a stem cell may be an ES cell, iPS cell, somatic stem cell (also called a tissue stem cell) or the like, but is not limited to these as long as it has the aforementioned abilities.

In this Description, a "pluripotent stem cell" is a stem cell having the ability to differentiate into various kinds of cells forming a living body, apart from placenta and other extra-embryonic tissue, and having self-replicating ability in an undifferentiated state. In this Description, a pluripotent stem cell may be an ES cell or iPS cell, but is not limited to these as long as it has the aforementioned abilities.

In this Description, the term "endodermal cell" refers to cells constituting the endoderm (hereunder sometimes called endoderm cells), cells constituting endodermally-derived tissue (hereunder sometimes called differentiated endodermal cells), and various somatic stem cells and precursor cells capable of differentiating into cells constituting endodermally-derived tissue (hereunder sometimes called endodermal stem cells or endodermal precursor cells). Examples include endoderm cells (typically embryonic endoderm cells), endodermally-derived somatic stem cells and precursor cells, and differentiated cells (mature cells) constituting endodermally-derived tissue.

The endodermally-derived tissue may be esophageal epithelium, gastric epithelium, gastrointestinal epithelium (duodenal epithelium, small-intestinal epithelium, large-intestinal epithelium, rectal epithelium), liver, pancreas, gallbladder, laryngeal epithelium, tracheal epithelium, lung, thyroid, thymus, bladder, urinary tract, eustachian tube or eardrum tissue or the like, but is not limited to these as long as it is tissue known at the time of this application to differentiate from endoderm. The endodermal stem cells (endodermal precursor cells) may be liver stem cells, liver precursor cells, liver blast cells, pancreatic precursor cells, intestinal epithelial precursor cells or the like, but similarly these cells are not limited to these as long as they are cells that are known at the time of this application to be various somatic stem cells and precursor cells capable of differentiating into cells constituting endodermally-derived tissue.

Moreover, in this Description a "liver precursor cell" is a cell that is more differentiated than an endoderm cell (typically, than an embryonic endoderm cell), and has the ability to differentiate into a hepatocyte.

The stem cell differentiation inducer capable of inducing differentiation of pluripotent stem cells into endodermal cells disclosed here is a composition containing as an active ingredient (that is, a substance contributing to inducing differentiation of pluripotent stem cells into endodermal cells) at least one kind of peptide (differentiation-inducing synthetic peptide) having differentiation inducing ability for inducing differentiation or promoting induction of differentiation into endodermal cells of specific pluripotent stem cells when supplied to a culture of such cells (typically, when added to medium in which such cells are cultured).

As discussed above, the differentiation-inducing synthetic peptide disclosed here is a synthetic peptide containing a stem cell differentiation-inducing peptide sequence that the inventors have found to induce differentiation of pluripotent stem cells into endodermal cells. This stem cell differentiation-inducing peptide sequence is selected from the signal peptide sequences of any proteins belonging to the APP family, the partial amino acid sequences of these signal peptide sequences (that is APP signal peptide-associated sequences), and modified amino acid sequences of these amino acid sequences.

A protein belonging to the APP family here is typically APP, APLP1 or APLP2. APP is implicated in the amyloid hypothesis—a hypothesis for the onset of Alzheimer's disease, while APLP1 and APLP2 are known as analogous proteins of APP.

SEQ ID NOS:1 to 6 represent signal peptide sequences of proteins in the APP family that are preferred for use in implementing the present invention.

Specifically, the amino acid sequence of SEQ ID NO:1 is an amino acid sequence consisting of a total of 29 amino acid residues constituting a human-derived APLP2 signal peptide.

The amino acid sequence of SEQ ID NO:2 is an amino acid sequence consisting of a total of 29 amino acid residues constituting a mouse-derived APLP2 signal peptide.

The amino acid sequence of SEQ ID NO:3 is an amino acid sequence consisting of a total of 38 amino acid residues constituting a human-derived APLP1 signal peptide.

The amino acid sequence of SEQ ID NO:4 is an amino acid sequence consisting of a total of 37 amino acid residues constituting a mouse-derived APLP1 signal peptide.

The amino acid sequence of SEQ ID NO:5 is an amino acid sequence consisting of a total of 17 amino acid residues constituting a human-derived APP signal peptide.

The amino acid sequence of SEQ ID NO:6 is an amino acid sequence consisting of a total of 17 amino acid residues constituting a mouse-derived APP signal peptide.

For constituting the differentiation-inducing synthetic peptide of the invention, the amino acid sequence of SEQ ID NOS:1 to 6 can be used as is as stem cell differentiation-inducing peptide sequences.

Although SEQ ID NOS:1 to 6 above represent APP, APLP1 or APLP2 signal peptide sequences from humans or mice, these sequences are only examples, and usable amino acid sequences are not limited to these. For example, various APP, APLP1 or APLP2 signal peptide sequences derived from rats, guinea pigs and other rodents, horses, donkeys and other Perissodactyla, pigs, cows and other Artiodactyla, chimpanzees, orangutans, macaques and other primates and the like (typically mammals) may be used.

A partial amino acid sequence having some of the continuous amino acid residues of a signal peptide of a protein in the APP family (hereunder sometimes called simply a partial amino acid sequence) may also be used as a stem cell differentiation-inducing peptide sequence. For example, a partial amino acid sequence having at least an amino acid sequence represented by SEQ ID NOS:16 to 25 can be used favorably as a stem cell differentiation-inducing peptide sequence.

In this Description, "having at least" means having specific continuous amino acid residues (typically, the amino acid residues represented by any of SEQ ID NOS:16 to 25) as an essential amino acid sequence, with additional C-terminal and N-terminal amino acid sequences being optional. That is, this partial amino acid sequence may be an amino acid sequence also having 1, 2, 3, 4 . . . or $X_c$ amino acid residues towards the C terminus and 1, 2, 3, 4 . . . or $X_N$ amino acid residues towards the N terminus from specific continuous amino acid residues (typically, the amino acid residues represented by any of SEQ ID NOS:16 to 25). The $X_c$ amino acid residue on the C-terminal side is the C-terminal amino acid residue of the full-length signal peptide sequence, and the $X_N$ amino acid residue on the N-terminal side is the N-terminal amino acid residue of the full-length signal peptide sequence.

Specifically, the amino acid sequences represented by SEQ ID NOS:16 to 25 are as follows.

The amino acid sequence represented by SEQ ID NO:16 is a partial amino acid sequence of the amino acid sequence represented by SEQ ID NO:1, and is an amino acid sequence consisting of 13 continuous amino acid residues from the #15 leucine residue to the #27 alanine residue counting from the N-terminal amino acid residue of that amino acid sequence.

The amino acid sequence represented by SEQ ID NO:17 is a partial amino acid sequence of the amino acid sequence represented by SEQ ID NO:2, and is an amino acid sequence consisting of 12 continuous amino acid residues from the #16 leucine residue to the #27 alanine residue counting from the N-terminal amino acid residue of that amino acid sequence.

The amino acid sequence represented by SEQ ID NO:18 is a partial amino acid sequence of the amino acid sequence represented by SEQ ID NO:3, and is an amino acid sequence consisting of 13 continuous amino acid residues from the #19 proline residue to the #31 leucine residue counting from the N-terminal amino acid residue of that amino acid sequence.

The amino acid sequence represented by SEQ ID NO:19 is a partial amino acid sequence of the amino acid sequence represented by SEQ ID NO:3, and is an amino acid sequence consisting of 13 continuous amino acid residues from the #26 leucine residue to the #38 glycine residue counting from the N-terminal amino acid residue of that amino acid sequence.

The amino acid sequence represented by SEQ ID NO:20 is a partial amino acid sequence of the amino acid sequence represented by SEQ ID NO:4, and is an amino acid sequence consisting of 13 continuous amino acid residues from the #18 proline residue to the #30 leucine residue counting from the N-terminal amino acid residue of that amino acid sequence.

The amino acid sequence represented by SEQ ID NO:21 is a partial amino acid sequence of the amino acid sequence represented by SEQ ID NO:4, and is an amino acid sequence consisting of 13 continuous amino acid residues from the #25 leucine residue to the #37 glycine residue counting from the N-terminal amino acid residue of that amino acid sequence.

The amino acid sequence represented by SEQ ID NO:22 is a partial amino acid sequence of the amino acid sequence represented by SEQ ID NO:5, and is an amino acid sequence consisting of 14 continuous amino acid residues from the #1 methionine residue to the #14 threonine residue counting from the N-terminal amino acid residue of that amino acid sequence.

The amino acid sequence represented by SEQ ID NO:23 is a partial amino acid sequence of the amino acid sequence represented by SEQ ID NO:5, and is an amino acid sequence consisting of 15 continuous amino acid residues from the #3 proline residue to the #17 alanine residue counting from the N-terminal amino acid residue of that amino acid sequence.

The amino acid sequence represented by SEQ ID NO:24 is a partial amino acid sequence of the amino acid sequence represented by SEQ ID NO:6, and is an amino acid sequence consisting of 14 continuous amino acid residues from the #1 methionine residue to the #14 threonine residue counting from the N-terminal amino acid residue of that amino acid sequence.

The amino acid sequence represented by SEQ ID NO:25 is a partial amino acid sequence of the amino acid sequence represented by SEQ ID NO:6, and is an amino acid sequence consisting of 15 continuous amino acid residues from the #3 proline residue to the #17 alanine residue counting from the N-terminal amino acid residue of that amino acid sequence.

The amino acid sequences of SEQ ID NO:27 and SEQ ID NO:28 are desirable examples of partial amino acid sequences having at least the amino acid sequence represented by SEQ ID NO:16 out of the stem cell differentiation-inducing peptide sequences.

The amino acid sequence represented by SEQ ID NO:27 is a partial amino acid sequence of the amino acid sequence represented by SEQ ID NO:1, and is an amino acid sequence consisting of a total of 23 amino acid residues from the #7 alanine residue to the #29 alanine residue counting from the N-terminal amino acid residue of that amino acid sequence. In other words, the amino acid sequence represented by SEQ ID NO:27 is a partial amino acid sequence of the amino acid sequence represented by SEQ ID NO:1, and is an amino acid sequence consisting of a total of 23 amino acid residues including an additional 8 amino acid residues at the N-terminal end of the amino acid sequence represented by SEQ ID NO:16 and an additional 2 amino acid residues at the C-terminal end of the amino acid sequence represented by SEQ ID NO:16.

The amino acid sequence represented by SEQ ID NO:28 is a partial amino acid sequence of the amino acid sequence represented by SEQ ID NO:1, and is an amino acid sequence consisting of a total of 16 amino acid residues from the #14 arginine residue to the #29 alanine residue counting from the N-terminal amino acid residue of that amino acid sequence. In other words, the amino acid sequence represented by SEQ ID NO:27 is a partial amino acid sequence of the amino acid sequence represented by SEQ ID NO:1, and is an amino acid sequence consisting of a total of 16 amino acid residues including an additional 1 amino acid residue at the N-terminal end of the amino acid sequence represented by SEQ ID NO:16, and an additional 2 amino acid residues at the C-terminal end of the amino acid sequence represented by SEQ ID NO:16.

The differentiation-inducing synthetic peptide disclosed here may also be a peptide consisting only of the aforementioned stem cell differentiation-inducing peptide sequence, but from the standpoint of improving stem cell differentiation-inducing activity, it is preferably a synthetic peptide having a transmembrane peptide sequence at the N-terminal or C-terminal end. Any amino acid sequence constituting a transmembrane peptide capable of passing through the cell membrane and/or nuclear membrane can be used as this transmembrane peptide sequence, without any particular limitations. Many desirable transmembrane peptide sequences are known, but amino acid sequences (including modified amino acid sequences) associated with NoLS (Nucleolar localization signals) are particularly desirable as amino acid sequences of the transmembrane peptide sequence of the differentiation-inducing synthetic peptide. Desirable examples of NoLS-associated transmembrane peptide sequences and other transmembrane peptide sequences (including modified amino acid sequences) are given by SEQ ID NOS:7 to 15. Specifically, these are as follows.

That is, the amino acid sequence of SEQ ID NO:7 corresponds to a NoLS consisting of a total of 13 amino acid residues from the #491 amino acid residue to the #503 amino acid residue of LIM Kinase 2, which is a kind of protein kinase present in human endothelial cells and associated with intracellular signaling.

The amino acid sequence of SEQ ID NO:8 corresponds to a NoLS consisting of a total of 14 amino acid residues derived from FGF2 (basic fibroblast growth factor).

The amino acid sequence of SEQ ID NO:9 corresponds to a NoLS consisting of a total of 8 amino acid residues contained in an N protein (nucleocapsid protein) of IBV (avian infectious bronchitis virus).

The amino acid sequence of SEQ ID NO:10 corresponds to a NoLS consisting of a total of 13 amino acid residues derived from adenovirus PTP (pre-terminal protein) 1 and PTP2.

The amino acid sequence of SEQ ID NO:11 corresponds to a transmembrane peptide sequence consisting of a total of 11 amino acid residues derived from a protein introduction domain contained in the TAT of HIV (Human Immunodeficiency Virus).

The amino acid sequence of SEQ ID NO:12 corresponds to a transmembrane peptide sequence consisting of a total of 11 amino acid residues of a protein introduction domain (PTD4) of a modified form of the TAT.

The amino acid sequence of SEQ ID NO:13 corresponds to a transmembrane peptide sequence consisting of a total of 16 amino acid residues derived from the ANT of Antennapedia, a mutant *Drosophila*.

The amino acid sequence of SEQ ID NO:14 corresponds to a transmembrane peptide sequence consisting of a total of 9 continuous arginine residues as a polyarginine.

The amino acid sequence of SEQ ID NO:15 corresponds to a transmembrane peptide sequence consisting of a total of 19 amino acid residues derived from a protein containing a MyoD (myoblast determination) family inhibiting domain.

The aforementioned transmembrane peptide sequences shown in the sequence tables are only examples, and usable peptide sequences are not limited to these. Various transmembrane peptide sequences that can be used in implementing the invention are described in various literature already published at the time of the present application. The amino acid sequences of these transmembrane peptide domains can be easily discovered by ordinary search techniques.

The amino acid sequence of SEQ ID NO:7 (including modified amino acid sequences), which is also described in Patent Literature 4, is particularly desirable as a transmembrane sequence. A synthetic peptide exhibiting strong stem cell differentiation-inducing properties can be obtained by combining the amino acid sequence of this SEQ ID NO:7 with the aforementioned stem cell differentiation-inducing peptide sequence.

It is especially desirable that the differentiation-inducing synthetic peptide disclosed here contain any of the following amino acid sequences:

```
                                       (SEQ ID NO: 26)
LLLLLLVGLTAPAGKKRTLRKNDRKKR (SEQ ID NO: 29)
MLPGLALLLLAAWTARAKKRTLRKNDRKKR (SEQ ID NO: 30)
AAAAATGRLLLLLLVGLTAPALAKKRTLRKNDRKKR (SEQ ID NO: 31)
RLLLLLLVGLTAPALAKKRTLRKNDRKKR (SEQ ID NO: 32)
MAATGTAAAAATGKLLVLLLLGLTAPAAAKKRTLRKNDRKKR (SEQ ID NO: 33)
MAATGTAAAAATGRLLLLLLVGLTAPALAKKRTLRKNDRKKR (SEQ ID NO: 34)
MGPASPAARGLSRRPGQPPLPLLLPLLLLLLRAQPAIGKKR

TLRKNDRKKR.
```

The amino acid sequence of SEQ ID NO:26 is an amino acid sequence consisting of a total of 27 amino acid residues, constructed by combining the amino acid sequence of SEQ ID NO:16, which is a partial amino acid sequence of an amino acid sequence (SEQ ID NO:1) constituting a signal peptide of human-derived APLP2, with the LIM kinase 2-derived amino acid sequence of SEQ ID NO:7 above via a single glycine residue (G) as a linker.

The amino acid sequence of SEQ ID NO:29 is an amino acid sequence consisting of a total of 30 amino acid residues, constructed by combining the amino acid sequence of SEQ ID NO:5, which constitutes a signal peptide of human-derived APP, contiguous with the LIM kinase 2-derived amino acid sequence of SEQ ID NO:7 above.

The amino acid sequence of SEQ ID NO:30 is an amino acid sequence consisting of a total of 36 amino acid residues, constructed by combining the amino acid sequence of SEQ ID NO:27, which is a partial amino acid sequence of an amino acid sequence (SEQ ID NO:1) constituting a signal peptide of human-derived APLP2, contiguous with the LIM kinase 2-derived amino acid sequence of SEQ ID NO:7 above.

The amino acid sequence of SEQ ID NO:31 is an amino acid sequence consisting of a total of 29 amino acid residues, constructed by combining the amino acid sequence of SEQ ID NO:28, which is a partial amino acid sequence of an amino acid sequence (SEQ ID NO:1) constituting a signal peptide of human-derived APLP2, contiguous with the LIM kinase 2-derived amino acid sequence of SEQ ID NO:7 above.

The amino acid sequence of SEQ ID NO:32 is an amino acid sequence consisting of a total of 42 amino acid residues, constructed by combining the amino acid sequence of SEQ ID NO:2, which constitutes a signal peptide of mouse-derived APLP2, contiguous with the LIM kinase 2-derived amino acid sequence of SEQ ID NO:7 above.

The amino acid sequence of SEQ ID NO:33 is an amino acid sequence consisting of a total of 42 amino acid residues, constructed by combining the amino acid sequence of SEQ ID NO:1, which constitutes a signal peptide of human-derived APLP2, contiguous with the LIM kinase 2-derived amino acid sequence of SEQ ID NO:7 above.

The amino acid sequence of SEQ ID NO:34 is an amino acid sequence consisting of a total of 51 amino acid residues, constructed by combining the amino acid sequence of SEQ ID NO:3, which constitutes a signal peptide of human-derived APLP1, contiguous with the LIM kinase 2-derived amino acid sequence of SEQ ID NO:7 above.

Some of the peptide chains (amino acid sequences) of the differentiation-inducing synthetic peptides disclosed here can be constructed by suitably combining such stem cell differentiation-inducing peptide sequences and transmembrane peptide sequences. Either the stem cell differentiation-inducing peptide sequence or the transmembrane peptide sequence can be disposed at the C end (N end). Also, the stem cell differentiation-inducing peptide sequence and the transmembrane peptide sequence are preferably arranged contiguous with each other. That is, preferably either no amino acid residues not belonging to the two sequences are disposed between the stem cell differentiation-inducing peptide sequence and the transmembrane peptide sequence, or the number of such residues is only about 1 to 3. For example, 1 or more (typically 2 or 3) amino acid residues (such as 1 or more glycine (G) residues) functioning as linkers may be included between the stem cell differentiation-inducing peptide sequence and the transmembrane peptide sequence.

Preferably at least one amino acid residue is amidated in the differentiation-inducing synthetic peptide disclosed here. The structural stability (such as protease resistance) of the synthetic peptide can be improved by amidating the carboxyl group of an amino acid residue (typically the C-terminal amino acid residue of the peptide chain).

A sequence (amino acid residue) part other than the amino acid sequences constituting the stem cell differentiation-inducing peptide sequence and transmembrane peptide sequence may be included as long as the stem cell differentiation-inducing activity is not compromised. Although not particularly limited, this partial amino acid sequence is preferably a sequence capable of maintaining the 3-dimensional shapes (typically linear shapes) of the stem cell differentiation-inducing peptide sequence and transmembrane peptide sequence. In the differentiation-inducing synthetic peptide, the total number of amino acid residues constituting the peptide chain may suitably be 100 or fewer, or preferably 60 or fewer, or more preferably 50 or fewer. A synthetic peptide of 30 or fewer amino acid residues is especially desirable.

A peptide with such a short chain is easy to chemically synthesize, so the differentiation-inducing synthetic peptide can be provided easily. The conformation (steric structure) of the peptide is not particularly limited as long as the stem cell differentiation-inducing ability for inducing differentiation of pluripotent stem cells into endodermal cells is obtained in the environment of use (in vitro or in vivo), but a linear or helix structure is preferred because it is less likely to produce an immunogen (antigen). A peptide with such a structure is unlikely to form an epitope. From this perspective, a differentiation-inducing synthetic peptide applied to a stem cell differentiation inducer is preferably a linear peptide with a relatively low molecular weight (typically 60 or fewer (especially 30 or fewer) amino acid residues).

The proportion of the stem cell differentiation-inducing peptide sequence and transmembrane peptide sequence as a percentage of the total amino acid sequence (that is, the number of amino acid residues constituting the stem cell differentiation-inducing peptide sequence and transmembrane peptide sequence as a percentage of the total amino acid residues constituting the peptide chain) is not particularly limited as long as the stem cell differentiation-inducing ability for inducing differentiation of pluripotent stem cells into endodermal cells is not compromised, but is preferably about 60% or more, or more preferably 80% or more, or especially 90% or more. A peptide consisting of the stem cell differentiation-inducing peptide sequence and transmembrane peptide sequence (that is, in which these sequences constitute 100% of the total amino acid sequence) is a preferred embodiment.

All of the amino acid residues are preferably L-amino acids in the differentiation-inducing synthetic peptide of the invention, but D-amino acids can be substituted for some or all of the amino acid residues as long as the stem cell differentiation-inducing ability for inducing differentiation of pluripotent stem cells into endodermal cells is not compromised.

The differentiation-inducing synthetic peptide disclosed here can be easily manufactured according to ordinary chemical synthesis methods. For example, any conventionally known solid-phase synthesis method or liquid-phase synthesis method may be used. Solid-phase synthesis using Boc (t-butyloxycarbonyl) or Fmoc (9-fluorenylmethoxycarbonyl) amino protecting groups is preferred.

For the differentiation-inducing synthetic peptide disclosed here, a peptide chain having the desired amino acid sequence and modifications (C-terminal amidation, etc.) can be synthesized by solid-phase synthesis using a commercial peptide synthesizer (available for example from Intavis AG or Protein Technologies).

The differentiation-inducing synthetic peptide may also be biosynthesized based on genetic engineering techniques. That is, a polynucleotide (typically DNA) is synthesized with a nucleotide sequence (including ATG initiation codon) coding for the amino acid sequence of the desired differentiation-inducing synthetic peptide. A recombinant vector having a genetic construct for expression consisting of the synthesized polynucleotide (DNA) and various regulatory elements for expressing the amino acid sequence in host cells (including promoters, ribosome-binding sites, terminators, enhancers, and various cis-elements for regulating expression levels) is constructed according to the host cells.

This recombinant vector is introduced into host cells (such as yeast, insect or plant cells) by ordinary methods, and the host cells or a tissue or body containing those cells is cultured under specific conditions. The target peptide is thus expressed and produced in the cells. The peptide is then isolated from the host cells (or medium if it has been excreted), and refolded and purified or the like as necessary to obtain the target differentiation-inducing synthetic peptide.

Methods conventionally used in the field may be adopted as the methods of constructing the recombinant vector and the methods of introducing the constructed recombinant vector into host cells and the like, and detailed explanations of these methods are omitted since they are not a feature of the present invention.

For example, a fused protein expression system may be used to achieve efficient large-scale production in host cells. That is, a gene (DNA) coding for the amino acid sequence of the desired differentiation-inducing synthetic peptide is chemically synthesized, and this synthetic gene is then introduced into a favorable site of a suitable fusion protein expression vector (for example, a GST (glutathione S-transferase) fusion protein expression vector such as the pET series provided by Novagen or the pGEX series provided by Amersham Biosciences). Host cells (typically *E. coli*) are then transformed with this vector. The resulting transformant is cultured to prepare the target fusion protein. Next, the protein is extracted and purified. The resulting purified fusion protein is then cleaved with a specific enzyme (protease) to release a target peptide fragment (the designed differentiation-inducing synthetic peptide), which is collected by a method such as affinity chromatography. It is also refolded as necessary by suitable methods. The differentiation-inducing synthetic peptide disclosed here can be manufactured using such a known conventional fusion protein expression system (such as a GST/His system provided by Amersham Biosciences).

Alternatively, template DNA for a cell-free protein synthesis system (that is a synthetic gene fragment containing a nucleotide sequence coding for the amino acid sequence of the differentiation-inducing synthetic peptide) can be constructed, and the target polypeptide can be synthesized in vitro by a cell-free protein synthesis system using various compounds necessary for peptide synthesis (ATP, RNA polymerase, amino acids, etc.). Cell-free protein synthesis systems are described for example in the papers of Shimizu et al (Shimizu et al., Nature Biotechnology, 19, 751-755 (2001)) and Madin et al (Madin et al., Proc. natl. Acad. Sci. USA, 97(2), 559-564 (2000)). At the time of this application, many companies are already involved in contract manufacturing polypeptides based on the techniques described in these papers, and cell-free protein synthesis kits (for example, the PROTEIOS® Wheat germ cell-free protein synthesis kit from CellFree Sciences Co., Ltd., Japan) are commercially available.

Nucleotide sequences coding for the differentiation-inducing synthetic peptide disclosed here and/or single- or double-stranded polypeptides containing nucleotide sequences complementary to these sequences may be easily manufactured (synthesized) by conventional known methods. That is, a nucleotide sequence corresponding to the amino acid sequence of the differentiation-inducing synthetic peptide can be easily determined and provided by selecting codons corresponding to each amino acid residue making up the designed amino acid sequence. Once the nucleotide sequence has been determined, a polynucleotide (single strand) corresponding to the desired nucleotide sequence can be easily obtained with a DNA synthesizer or the like. The resulting single-stranded DNA can then be used as a template to obtain the target double-stranded DNA by various enzymatic synthesis techniques (typically PCR). The polynucleotide may be in the form of either DNA or RNA (mRNA or the like). The DNA may be provided in either double-stranded or single-stranded form. If single-stranded, it may be either a coding strand (sense strand) or a non-coding strand (antisense stranded) with a sequence complementary to the coding strand.

As discussed above, the resulting polynucleotide can then be used as a material to construct a recombinant gene (expression cassette) for producing the differentiation-inducing peptide in various host cells or with a cell-free protein synthesis system.

The differentiation-inducing synthetic peptide disclosed here may also be in the form of a salt as long as the stem cell differentiation-inducing activity is not compromised. For example, it is possible to use an acid addition salt of the peptide obtained by adding and reacting a commonly used inorganic acid or organic acid by ordinary methods. Other salts (such as metal salts) are also possible as long as the stem-cell differentiation-inducing activity is retained. Thus, the term "peptide" described in this Description and Claims encompasses these salts.

The stem cell differentiation inducer disclosed here may also contain various pharmaceutically (medicinally) acceptable carriers according to the form of use as long as the differentiation-inducing synthetic peptide that is its active ingredient is retained without comprising its stem cell differentiation-inducing activity. Diluents, and excipients and the like are preferably those commonly used in peptide drugs. These may differ depending on the use and form of the stem cell differentiation inducer, but typical examples include water, physiological buffer solution and various organic solvents. Aqueous alcohol (ethanol, etc.) solutions of suitable concentrations, glycerol, and olive oil and other non-drying oils are also possible, as are liposomes. Examples of other accessory ingredients that may be contained in the stem cell differentiation inducer include various fillers, extenders, binders, humectants, surfactants, colorants, perfumes and the like.

The form of the stem cell differentiation inducer is not particularly limited. For example, typical forms include liquids, suspensions, emulsions, aerosols, foams, granules, powders, tablets, capsules, ointments, aqueous gels and the like. It may also be in the form of a freeze-dried preparation or granules to be dissolved in physiological saline or a suitable buffer (such as PBS) or the like before use to prepare a liquid.

The specific processes for preparing drugs (compositions) of various forms using the differentiation-inducing synthetic peptide (principal ingredient) and various carriers (accessory ingredients) as materials can be in accordance with conventional known methods, and these preparation methods are not explained in detail because they are not a feature of the invention. An example of a detailed information source for formulations is Comprehensive Medicinal Chemistry, Corwin Hansch, ed., Pergamon Press (1990). The entire contents of this book are incorporated by reference in this Description.

The pluripotent stem cells to which the stem cell differentiation inducer (differentiation-inducing synthetic peptide) disclosed here is applied are not particularly limited, and the inducer can induce differentiation (or promote induction of differentiation) of various pluripotent stem cells into endodermal cells. Examples include ES cells and iPS cells from humans and non-human animals (typically vertebrates, especially mammals). iPS cells are especially preferred for application of the stem cell differentiation inducer (differentiation-inducing synthetic peptide) disclosed here.

The stem cell differentiation inducer (differentiation-inducing synthetic peptide) disclosed here can be used by methods and in dosages suited to its form and purpose.

For example, to induce differentiation of pluripotent stem cells (such as an iPS cell strain) cultured (passaged) in vitro, a suitable amount of the stem cell differentiation inducer (differentiation-inducing synthetic peptide) disclosed here can be added to medium to induce differentiation of the pluripotent stem cells at any stage of the culture process (preferably after a specific period of culture (proliferation) or passage with the cells maintained in an undifferentiated state). The added amount and number of additions are not particularly limited since they may differ depending on various conditions, including the type of cultured cells, cell density (cell density at the beginning of culture), number of passages, culture conditions, type of medium and the like. When culturing pluripotent stem cells, the number of additions is preferably 1 to several (such as at beginning of culture followed by further additions at the time of cell passage or medium replacement) so that the concentration of the differentiation-inducing synthetic peptide in the medium is within the range of about 0.1 µM to 100 µM, or preferably 0.5 µM to 20 µM (such as 1 µM to 10 µM).

Moreover depending on the type and purpose of the target pluripotent stem cells (type of endodermal cells targeted for differentiation induction, for example), the stem cell differentiation inducer (differentiation-inducing synthetic peptide) disclosed here may be used in combination with another cell differentiation-inducing factor. Examples of this cell differentiation-inducing factor include retinoic acid, various osteogenic factors (factors in the BMP family), activin and other factors in the TGF-β superfamily, basic fibroblast growth factor (bFGF), acidic fibroblast growth factor (aFGF) and other factors in the FGF superfamily, leukemia inhibitory factor (LIF), cholinergic differentiation factor (CDF), ciliary neurotrophic factor (CNTF) and other factors in the cytokine family, and various interleukins, tumor necrosis factor (TNF-α), interferon γ (IFNγ), hepatocyte growth factor (HGF) and the like.

The target endodermal cells (and thus differentiated cells, tissues, organs and the like) can also be efficiently induced to differentiate (produced) from pluripotent stem cells (such as iPS cells or ES cells) cultured (passaged) in vitro. That is, using the differentiation induction method disclosed here (in vitro method for producing endodermal cells or tissues or organs grown from such endodermal cells), repair or regeneration can be efficiently accomplished in a patient requiring repair or regeneration by returning target endodermal cells that have been efficiently induced to differentiate in vitro (or a tissue body or the like grown from such endodermal cells) to a site (the interior of the patient body) requiring repair or regeneration. It is thus possible to efficiently treat various diseases for which tissue body regeneration is an efficient treatment. Moreover, endodermal cells that have been induced to differentiate in vitro by the differentiation induction method disclosed here can be used as medical materials for treating liver failure, liver cancer, diabetes, pancreatic cancer, digestive cancers and other conditions involving endodermally-derived tissue (typically, dysfunction of such tissue) as well as tissue injury from a regenerative medicine approach.

The efficiency and accuracy of evaluation can also be improved and costs reduced if liver precursor cells or hepatocytes that have been induced to differentiate in large quantities by in vitro culture are used to evaluate drug toxicity and effectiveness. Biosynthesis products, typically excreted proteins, hormones and other physiologically active substances (such as insulin and the like) can also be produced using endodermal cells (such as pancreatic cells) that have been induced to differentiate in large quantities by in vitro culture.

Moreover, by testing endodermal cell materials (endodermal cells or cell masses or tissues containing endodermal cells) that have been induced to differentiate in large quantities by in vitro culture, it is possible to perform tests that have been difficult to perform in the past. For clarifying patient conditions and in the field of drug research and development for example, efficient research is possible using endodermal cell materials that have been induced to differentiate from human-derived pluripotent stem cells.

As is obvious from the above explanation, using any of the differentiation-inducing synthetic peptides disclosed here, the present invention can also provide cells or a cell mass, tissue, organ or the like that has been induced to differentiate from endodermal cells.

Some examples of the present invention are explained here, but not with the intent of restricting the invention to these examples.

Example 1: Peptide Synthesis

Seven kinds of synthetic peptides consisting of the respective amino acid sequences of SEQ ID NO:26 and SEQ ID NOS:29 to 34 were manufactured with the peptide synthesizer described below. In the following explanations, these synthetic peptides are called Sample 1 through Sample 7 in the order of the sequence numbers. Table 1 lists the amino acid sequences and other data for these synthetic peptides.

TABLE 1

| Sample No. | Amino acid sequence | Total amino acid residues |
|---|---|---|
| 1 | LLLLLLVGLTAPAGKKRTLRKNDRKKR-CONH2 (SEQ ID O: 26) | 27 |
| 2 | MLPGLALLLLAAWTARAKKRTLRKNDRKKR-CONH2 (SEQ ID NO: 29) | 30 |

TABLE 1-continued

| Sample No. | Amino acid sequence | Total amino acid residues |
|---|---|---|
| 3 | AAAAATGRLLLLLLVGLTAPALAKKRTLRKNDRKKR-COOH (SEQ ID NO: 30) | 36 |
| 4 | RLLLLLLVGLTAPALAKKRTLRKNDRKKR-COOH (SEQ ID NO: 31) | 29 |
| 5 | MAATGTAAAAATGKLLVLLLLGLTAPAAAKKRTLRKNDRKKR-COOH (SEQ ID NO: 32) | 42 |
| 6 | MAATGTAAAAATGRLLLLLLVGLTAPALAKKRTLRKNDRKKR-COOH (SEQ ID NO: 33) | 42 |
| 7 | MGPASPAARGLSRRPGQPPLPLLLPLLLLLLRAQPAIGKKRTLRKNDRKKR-COOH (SEQ ID NO: 34) | 51 |

As shown in Table 1, the peptides of each sample has an amino acid sequence (SEQ ID NO:7) derived from LIM kinase 2 as a transmembrane peptide sequence at the C end of the peptide chain, and a stem cell differentiation-inducing peptide sequence at the N end, either contiguous with the other sequence or with a linker region consisting of one glycine (G) residue between the two.

Specifically, Sample 1 is an amino acid sequence consisting of a total of 27 amino acid residues, having a partial amino acid sequence (SEQ ID NO:16) of an amino acid sequence constituting a signal peptide of human-derived APLP2 as a stem cell differentiation inducing peptide sequence at the N end, and an LIM kinase 2-derived amino acid sequence (SEQ ID NO:7) as a transmembrane peptide sequence at the C end, with a linker region consisting of one glycine (G) residue between the two. In the peptide of this Sample 1, the carboxyl (—COOH) of the C-terminal amino acid is amidated (—CONH$_2$).

Sample 2 is an amino acid sequence consisting of a total of 30 amino acid residues, having an amino acid sequence (SEQ ID NO:5) constituting a signal peptide of human-derived APP as a stem cell differentiation-inducing peptide sequence at the N end, contiguous with an LIM kinase 2-derived amino acid sequence (SEQ ID NO:7) as transmembrane peptide sequence at the C end. In the peptide of this Sample 2, the carboxyl (—COOH) of the C-terminal amino acid is amidated (—CONH$_2$).

Sample 3 is an amino acid sequence consisting of a total of 36 amino acid residues, having a partial amino acid sequence (SEQ ID NO:27) of an amino acid sequence constituting a signal peptide of APLP2 as a stem cell differentiation-inducing peptide sequence at the N end, contiguous with an LIM kinase 2-derived amino acid sequence (SEQ ID NO:7) as transmembrane peptide sequence at the C end.

Sample 4 is an amino acid sequence consisting of a total of 29 amino acid residues, having a partial amino acid sequence (SEQ ID NO:28) of an amino acid sequence constituting a signal peptide of APLP2 as a stem cell differentiation-inducing peptide sequence at the N end, contiguous with an LIM kinase 2-derived amino acid sequence (SEQ ID NO:7) as transmembrane peptide sequence at the C end.

Sample 5 is an amino is an amino acid sequence consisting of a total of 42 amino acid residues, having an amino acid sequence (SEQ ID NO:2) constituting a mouse-derived APLP2 signal peptide as a stem cell differentiation-inducing peptide sequence at the N end, contiguous with an LIM kinase 2-derived amino acid sequence (SEQ ID NO:7) as transmembrane peptide sequence at the C end.

Sample 6 is an amino acid sequence consisting of a total of 42 amino acid residues, having an amino acid sequence (SEQ ID NO:1) constituting a human-derived APLP2 signal peptide as a stem cell differentiation-inducing peptide sequence at the N end, contiguous with an LIM kinase 2-derived amino acid sequence (SEQ ID NO:7) as transmembrane peptide sequence at the C end.

Sample 7 is an amino acid sequence consisting of a total of 51 amino acid residues, having an amino acid sequence (SEQ ID NO:3) constituting a human-derived APLP1 signal peptide as a stem cell differentiation-inducing peptide sequence at the N end, contiguous with an LIM kinase 2-derived amino acid sequence (SEQ ID NO:7) as transmembrane peptide sequence at the C end.

The peptides of Samples 1 to 7 are all linear peptides. All of these peptides were synthesized by solid-phase synthesis (Fmoc method) using a commercial peptide synthesizer (Intavis AG Co.) according to the manual. The mode of use of the peptide is not explained in detail because it is not a feature of the invention.

The synthesized peptides were dissolved in a solvent consisting of 1 volume of DMSO mixed with 1 volume of ethanol (DMSO/EtOH=1/1) to prepare a stock solution.

Example 2: Test to Evaluate Stem Cell Differentiation-Inducing Activity of Differentiation-Inducing Synthetic Peptide Based on iPS Cell Transformation The differentiation-inducing activity of a differentiation-inducing synthetic peptide (Sample 1) obtained in Example 1 above was evaluated based on the transformation of iPS cells cultured and passaged in vitro. A peptide-free group was also provided as a comparative example. The details of the evaluation test were as follows.

Cells supplied by the Kyoto University Center for iPS cell Research and Application were used as the human-derived iPS cells in this example (clone name: 201B2 or 201B7, reference source: Takahashi K et al., Cell, 131, 861-872 (2007)). For the feeder cells used in culturing these iPS cells, mouse embryonic fibroblasts (MEF cells) were used to passage (maintain) the iPS cells, while mouse embryonic fibroblasts (cell strain SNL 76/7) supplied under license by the Baylor College of Medicine were used in testing to evaluate the stem cell differentiation-inducing activity of the differentiation-inducing synthetic peptide (Sample 1).

Feeder cells that had been inactivated by mitomycin C treatment were seeded ahead of time on a gelatin-coated 24-well plate 1 to 4 days before seeding of the iPS cells. Immediately before seeding of the iPS on the feeder cells, the feeder cells were washed with PBS(−) (phosphate-buffered saline), and 0.5 mL/well of ESC medium (DMEM-F12 medium containing 15% KSR (Knockout® Serum Replacement: Life Technologies), 2 mM L-glutamine, 1% nonessential amino acids, 0.1 mM 2-mercaptoethanol, 50 units/mL penicillin, 50 µg/mL streptomycin) was substituted to prepare feeder cells for evaluation.

The iPS cells were passaged and maintained on mitomycin C-treated MEF cells until the suitable cell numbers were obtained on one or two 6 cm culture plates. These iPS cells were subjected to dissociation treatment with CTK solution (0.25% trypsin solution containing 0.1 mg/mL collagenase IV (Life Technologies), 1 mM calcium chloride and 20% KSR) until the edges of the iPS cell colonies became detached. The CTK solution was washed and removed with PBS(−), 2 mL of ESC medium was added, and the iPS cell colonies were completely detached with a cell scraper. The ESC medium in the culture dish with the iPS colonies suspended therein was transferred to a 15 mL centrifuge tube, and the iPS colonies remaining in the culture dish were washed out with ESC medium and collected in the same 15 mL tube. This 15 mL tube was left standing for 5 minutes to precipitate the iPS cell colonies, the supernatant was removed, and the iPS cell colonies were dispersed and suspended by pipetting in new ESC medium to prepare an iPS cell suspension. This iPS cell suspension was seeded 0.5 mL/well on SNL 76/7 feeder cells prepared as described above. Sample 1 that had been prepared with DMSO/EtOH=1/1 to a peptide concentration of 2 mM was then added 2.0 µL/well (that is, to a peptide concentration of 4.0 µM in the well), and the iPS cells were cultured under conditions of 37° C., 5% $CO_2$. A peptide-free group with no peptide added was established as a control group.

The medium was replaced and peptide was added two days, four days and six days after initiation of iPS cell culture. Specifically, medium was removed from each well, 1 mL of new ESC medium was added per well, and Sample 1 that had been adjusted with DMSO/EtOH=1/1 medium to a peptide concentration of 2 mM was added 2.0 µL/well. Culture was performed with the peptide for a total of 7 days after initiation of iPS cell culture. After the seventh day, only the medium was replaced every two days, and culture was continued for an optional period.

Figure 2:
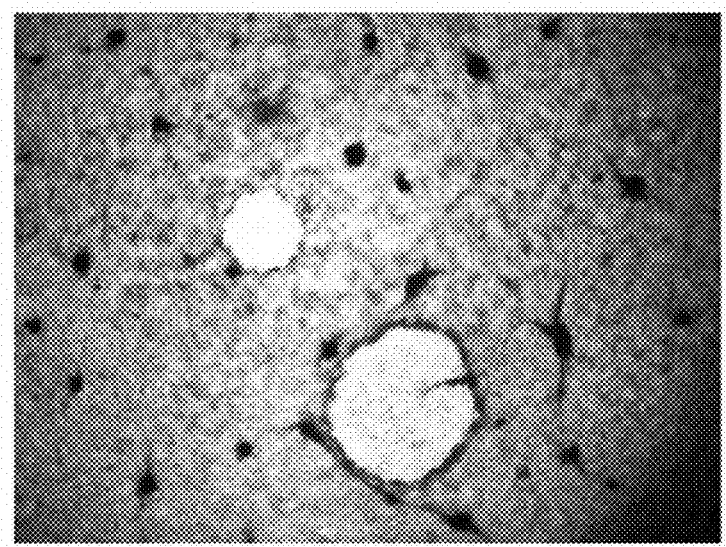
FIG. 2 is an optical microscope image showing the structure of iPS cells cultured without addition of a differentiation-inducing synthetic peptide.

FIGS. 1 and 2 show the results of microscopic observation of the morphology of the cultured iPS cells eight days after the beginning of culture. The iPS cells cultured for this period have proliferated while forming colonies, and adjacent colonies have fused together. Differentiated iPS cells or in other words colonies made up of such cells show increased transparency to light due to morphological changes (specifically, enlargement of the cytoplasm), and appear white under an optical microscope. Meanwhile, undifferentiated iPS cells or in other words colonies made up of such cells appear black under an optical microscope because they have low optical transparency.

In the peptide-free group, as shown in FIG. 2, most of the microscope field (80% or more) appears black under the microscope, confirming that it is occupied by colonies of undifferentiated iPS cells. One or two white-looking differentiated colonies also appear in the field. The number of differentiated colonies increases as the culture time is prolonged. These differentiated colonies are colonies composed of iPS cells that have differentiated naturally as the culture time is prolonged under the peptide-free culture conditions of this example.

In the Sample 1 group, on the other hand, as shown in FIG. 1, most of the microscope field (80% or more) appears white under the microscope, confirming that it is occupied by colonies of differentiated iPS cells. A comparison of FIGS. 1 and 2 provides visual confirmation that the differentiation-inducing synthetic peptide disclosed here (and thus a stem cell differentiation inducer containing this peptide) dramatically promotes differentiation induction.

Example 3: Test to Evaluate Stem Cell Differentiation-Inducing Activity of Differentiation-Inducing Synthetic Peptide by Quantitative RT-PCR The stem cell differentiation-inducing activity of a differentiation-inducing synthetic peptide (Sample 1) obtained in Example 1 above was evaluated by measuring changes over time in the expressed amounts of a stem cell differentiation marker gene (that is, a stem cell marker gene) and differentiation marker genes for the three kinds of germ layer cells. iPS cells that had been cultured and passaged in vitro were used as the test cells. The specifics of the evaluation test were as follows.

iPS cells (clone name: 201B2 or 201B7) were cultured as in Example 2 except that Sample 1 that had been prepared with DMSO/EtOH=1/1 to a peptide concentration of 4 mM was added 1.5 µL/well (that is to a peptide concentration of 6.0 µM in the well). A peptide-free group was also established as a comparative example. The medium was replaced and peptide was added two days, four days and six days after initiation of iPS cell culture. Specifically, medium was removed from each well, 1 mL of new ESC medium was added per well, and Sample 1 that had been adjusted with DMSO/EtOH=1/1 medium to a peptide concentration of 4 mM was added 1.5 µL/well (that is to a peptide concentration of 6.0 µM in the well). Culture was performed with the peptide for a total of 7 days after initiation of iPS cell culture. After the seventh day, only the medium was replaced every two days, and culture was continued for an optional period.

iPS cells were collected on arbitrary days after initiation of iPS cell culture, and iPS cell RNA was extracted with a commercial RNA extraction and purification kit (High Pure RNA Isolation Kit: Roche Applied Science). All operations were performed without RNAse, in accordance with the manual attached to the kit. The purified RNA was assayed by measuring absorbency.

25 to 50 µg of purified RNA was supplied to quantitative RT-PCR, and the expressed amounts of a stem cell marker gene and differentiation marker genes for the three kinds of germ layer cells were quantified. Specifically, the expressed amounts of the Oct 3/4 gene as a stem cell marker gene, the NES gene as an ectodermal cell differentiation marker gene (that is, an ectodermal cell marker gene), the Bry gene as a mesodermal cell differentiation marker gene (that is, a mesodermal cell marker gene) and the GATA4, SOX17, FOXA2 and AFP genes as endodermal cell differentiation marker genes (that is, endodermal cell marker genes) were investigated. The GAPDH gene was also adopted as a housekeeping gene (endogenous control). A One Step SYBR® PrimeScript® PLUS RT-PCR Kit (TaKaRa Bio) was used for the quantitative RT-PCR, in accordance with the attached manual. An ABI Prism® 7700 (Life Technologies) was used as the real time PCR system. Primers were obtained using a Perfect Real Time support system (TaKaRa Bio). The quantitative RT-PCR reaction consisted of 5 minutes of incubation at 42° C. to perform reverse transcription, followed by 10 seconds of incubation at 95° C., and 40 cycles consisting of 5 seconds at 95° and 31 seconds at 63° C. The primers used in RT-PCR are shown in Table 2.

TABLE 2

| Differentiation marker gene | Primer set ID |
|---|---|
| Oct 3/4 gene (POU5F1 gene) | HA172344 |
| NES gene | HA042877 |
| Bry gene (T gene) | HA147738 |
| GATA4 gene | HA176241 |
| SOX17 gene | HA162472 |
| FOXA2 gene | HA155227 |
| AFP gene | HA184905 |
| GAPDH gene | HA067812 |

Figure 3:
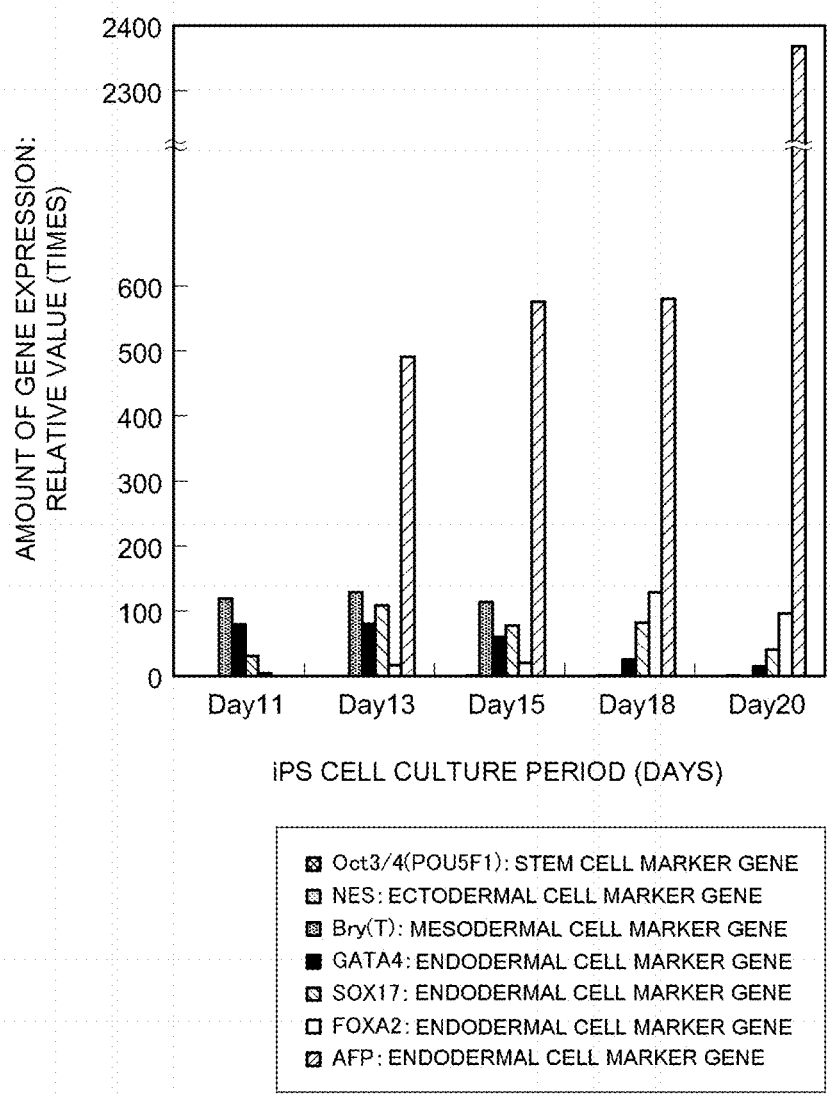
FIG. 3 is a graph showing quantitative results for expression of a stem cell differentiation marker gene and differentiation marker genes for the three kinds of germ layer cells in iPS cells cultured after addition of a differentiation-inducing synthetic peptide of one embodiment. The horizontal axis of the graph shows a period of culturing (days), while the vertical axis shows the amount of expression of each gene in the peptide-addition group as a relative value relative to expression in the peptide-free group.

The quantitative results for expression of a stem cell marker gene and differentiation marker genes for the three kinds of germ layer cells are shown in FIG. 3. The expressed amounts of these genes were first corrected by the expressed amounts of the GAPDH gene in each test group, and the relative expressed amount of the gene in the Sample 1 group relative to the expressed amount of the gene in the peptide-free group was determined by the ΔΔCt method.

As shown in FIG. 3, beginning 13 days after initiation of culture the relative expressed amount of the AFP gene (endodermal marker gene) in iPS cells of the Sample 1 group was confirmed to have increased much more than the relative expressed amounts of the other genes. The increase in the relative expressed amount of the AFP gene in iPS cells in the Sample 1 group was found to be particularly dramatic on the 20th day after initiation of culture. These results show that the differentiation-inducing synthetic peptide disclosed here (and thus the stem cell differentiation inducer containing this peptide) has the stem cell differentiation-inducing ability to differentiate pluripotent stem cells in an undifferentiated state into endodermal cells.

The AFP endodermal marker gene (and AFP itself) is a gene (protein) known as a liver precursor cell differentiation marker gene (and differentiation marker protein), and changes over time in expression of both the gene and the protein have often been in the literature with the aim of understanding the process of differentiation of pluripotent stem cells into liver precursor cells and hepatocytes (Non-patent Literature 1, 2). Thus, these results show that the differentiation-inducing synthetic peptide disclosed here (and thus the stem cell differentiation inducer containing this peptide) has the stem cell differentiation-inducing ability to differentiate pluripotent stem cells in an undifferentiated state into liver precursor cells.

Example 4: Test to Evaluate Expressed Amounts of AFP and ALB in Relation to the Stem Cell Differentiation-Inducing Activity of the Differentiation-Inducing Synthetic Peptide The stem cell differentiation-inducing activity of the differentiation-inducing synthetic peptide (Sample 1) obtained in Example 1 was evaluated by quantifying changes over time in the expressed amounts (typically extracellular secretion) of AFP and ALB, which are proteins known as markers of differentiation into endodermal cells. It is known that AFP is expressed in cells that have differentiated into liver precursor cells among the endodermal cells, while ALB is expressed in cells that have differentiated sufficiently to function effectively as hepatocytes (that is, hepatocytes or hepatocyte-like cells). That is, of the endodermal cell differentiation markers in this example, AFP was adopted as a differentiation marker protein for liver precursor cells, and ALB as a differentiation marker protein for hepatocytes (or hepatocyte-like cells). iPS cells that had been cultured and passaged in vitro were used as the test cells. The details of the evaluation test are as follows.

iPS cells (clone name: 201B2 or 201B7) of the Sample 1 group (peptide concentration in medium 6 μM) and peptide-free group (comparative example) were cultured as in Example 3. On arbitrary days after initiation of iPS cell culture, parts of the culture liquids (culture supernatants) of the cultured Sample 1 group and peptide-free group iPS cells were collected and stored at −80° C.

The collected culture supernatants were supplied to enzyme-linked immunoassay (called EIA or ELISA) for detecting AFP and ALB, to assay the AFP and ALB concentrations of each culture supernatant. The AFP ELISA was accomplished with a Quantikine ELISA Human AFP (R&D Systems, Inc.), and the ALB ELISA with an Albumin Human ELISA kit (Abcam plc) in accordance with the attached manuals.

The AFP ELISA is explained first. Specifically, human AFP standard protein solution diluted to from 0.12 to 7.5 ng/mL was prepared for the calibration curve samples, ESC medium as a blank sample, and the aforementioned culture supernatant diluted from 40× to 640× with ESC medium for the evaluation samples. 100 μL of the accessory diluent was added to ELISA wells, and 50 μL of each of the respective samples was added to an ELISA well, and left standing for 2 hours at room temperature. After the specified amount of time, the samples were removed from the ELISA wells, which were then washed four times with washing buffer. 200 μL of the accessory labeled antibody solution was added per well, and left standing for two hours at room temperature. After the specified amount of time, the antibody solution was removed from the wells, which were then washed four times with washing buffer.

200 μL of a substrate solution obtained by mixing 1 volume each of the accessory coloring reagent (A) and coloring reagent (B) was added per well, and left standing for 30 minutes in the dark. After the specified amount of time, 50 μL of the accessory reaction termination solution was added per well to terminate the coloring reaction. Absorbance $A_{450}$ at 450 nm and absorbance $A_{550}$ at 550 nm were then measured with a spectrophotometer in the reaction liquid in the wells.

The ALB ELISA is explained next. Specifically, human ALB standard protein solution diluted to from 3.13 to 100 ng/mL was prepared for the calibration curve samples, ESC medium as a blank sample, and the aforementioned culture supernatant diluted from 1× to 10× with ESC medium for the evaluation samples. 50 μL of each sample was added to an ELISA well, and left standing for one hour at room temperature. After the specified amount of time, the samples were removed from the ELISA wells, which were then washed four times with washing buffer. 50 μL of the accessory 1× Biotinylated Albumin Antibody (biotinylated antibody solution) was then added to each well, and left standing for 30 minutes at room temperature. After the specified amount of time, the antibody solution was removed from the wells, which were then washed four times with washing buffer. 50 μL of the accessory 1×SP Conjugate (avidin-labeled antibody solution) was then added to each well, and left standing for 30 minutes at room temperature. After the specified amount of time, the antibody solution was removed from the wells, which were then washed four times with washing buffer.

50 μL of the accessory Chromogen Substrate Solution (coloring reagent) was then added per well, and left standing for 15 minutes in the dark. After the specified amount of time, 50 μL of the accessory reaction termination solution was added to each well to terminate the coloring reaction. Absorbance $A_{450}$ at 450 nm and absorbance $A_{550}$ at 550 nm were then measured with a spectrophotometer in the reaction liquid in the wells.

Absorbance values $A_{(450-550)}$ were calculated by subtracting the absorbance $A_{550}$ from the absorbance $A_{450}$ obtained by the previous measurement (that is, absorbance $A_{(450-550)}$= absorbance $A_{550}$–absorbance $A_{450}$) for each of the samples from the AFP evaluation test group and ALB evaluation test group. For each of the AFP evaluation test group and ALB evaluation test group, calibration curves were then prepared from the absorbance $A_{(450-550)}$ values of the calibration curve samples, and the AFP concentrations (ng/mL) and ALB concentrations (ng/mL) in the culture supernatants of each test group were calculated from the calibration curves and the absorbance values $A_{(450-550)}$ of the evaluation samples. The results are shown in FIG. 4.

Figure 4:
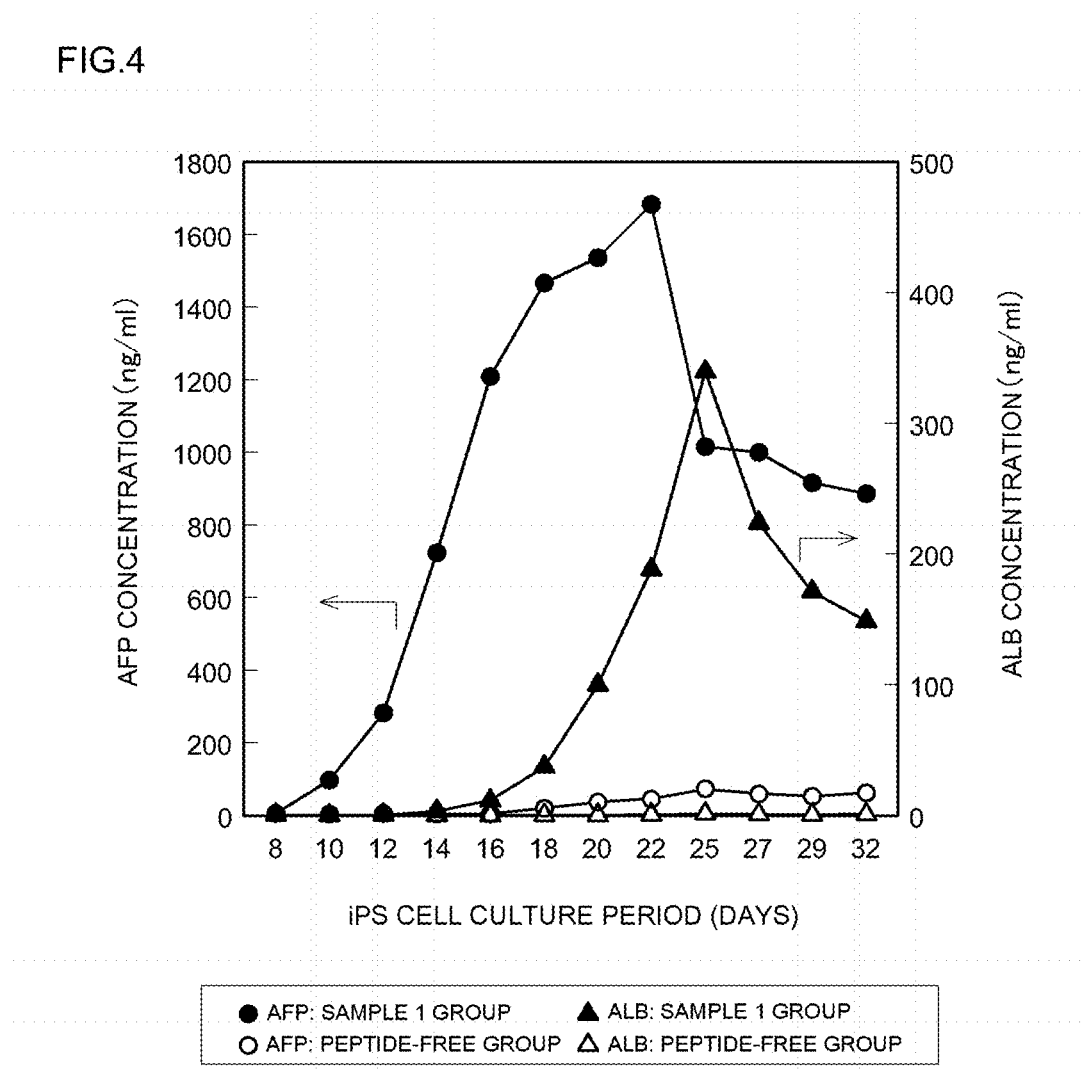
FIG. 4 is a graph showing results from a measurement of AFP and ALB levels in culture supernatant of iPS cells cultured after addition of a differentiation-inducing synthetic peptide of one embodiment.

As shown in FIG. 4, in comparison with the AFP level of the culture supernatant collected from the peptide-free group with the same culture time, the AFP level of the culture supernatant collected from the Sample 1 group increased dramatically as the culture time increased beginning around the 8th day after initiation of iPS cell culture, peaked on the 22nd day after initiation of culture, and then decreased as the culture time progressed.

The amount of AFP secretion (AFP expression) in liver precursor cells is known to change according to the differentiation stage of the liver precursor cells. Specifically, cells at an earlier stage of differentiation (cells with a low degree of differentiation, liver precursor cells similar to endodermal cells, poorly-differentiated cells) have low AFP expression, but AFP expression increases as the differentiation stage progresses, while cells at a later differentiation stage (cells with a high degree of differentiation, liver precursor cells similar to hepatocytes, highly-differentiated cells) express less AFP. The dramatic increase in the AFP level of the culture supernatant collected from the Sample 1 group and the subsequent decrease are consistent with the transition in AFP levels accompanying progressive stages of differentiation of such liver precursor cells.

Moreover, as shown in FIG. 4, in comparison with the ALB level of the culture supernatant collected from the peptide-free group with the same culture time, the ALB level of the culture supernatant from the Sample 1 group increased dramatically as the culture time increased beginning around the 16th day after initiation of iPS culture, peaked on the 25th day after initiation of culture, and then decreased as the culture time progressed.

It is known that in the process of differentiation of endodermal cells into hepatocytes, ALB begins to be expressed later than AFP, but as the differentiation stage progresses the amount of ALB excretion (in other words the amount of ALB expression) increases, after which ALB excretion gradually decreases. As discussed above, the pattern of ALB expression, in which ALB began to be expressed later than AFP, increased dramatically and then decreased gradually in the culture supernatant collected from the Sample 1 group, is consistent with the changes in ALB expression accompanying the progressive stages of differentiation from endodermal cells to hepatocytes.

The results above show that the differentiation-inducing synthetic peptide disclosed here (and thus the stem cell differentiation inducer containing this peptide) has the stem cell differentiation-inducing activity to differentiate pluripotent stem cells in an undifferentiated stage into endodermal cells. These results also show that the differentiation-inducing synthetic peptide disclosed here (and thus the stem cell differentiation inducer containing this peptide) has the stem cell differentiation-inducing activity to differentiating pluripotent stem cells in an undifferentiated state into liver precursor cells and hepatocytes (hepatocyte-like cells).

Moreover, it was confirmed that the iPS cells in the Sample 1 group expressed the endodermal cell marker genes (also known as endodermal marker genes) SOX17, GATA4 and FOXA2 sooner than the AFP gene (see FIG. 3). Changes in the expression of these marker genes (marker gene expression profiles) indicate that the iPS cells in the Sample 1 group have been induced to differentiate first into endodermal cells (typically, embryonic endoderm cells). Since these cells expressing endodermal cell marker genes also differentiated into more highly differentiated endodermal cells (that is, liver precursor cells and hepatocytes) as the culture time progressed (Examples 3, 4), it is clear that these cells expressing endodermal cell marker genes are in fact endodermal cells. This shows that the differentiation-inducing synthetic peptide disclosed here (and thus the stem cell differentiation inducer containing this peptide) has the stem cell differentiation inducing activity to differentiate pluripotent stem cells in an undifferentiated state into endodermal cells (typically embryonic endoderm cells).

Example 5: Test to Evaluate AFP Expression Associated with Stem Cell Differentiation-Inducing Activity of Differentiation-Inducing Synthetic Peptide The stem cell differentiation-inducing activities of the differentiation-inducing synthetic peptides (Samples 2-7) obtained in Example 1 above were evaluated by measuring changes over time in AFP expression levels (typically, extracellular excretion levels). AFP is a differentiation marker protein that is known to be in expressed in cells that have differentiated into liver precursor cells in particular of the endodermal cells. iPS cells that had been cultured and passaged in vitro were used as the test cells. The details of the evaluation test are as follows.

As in Example 3, the peptides of Samples 2 through 7 were added to a peptide concentration of 6.0 µM to added to medium containing cultured iPS cells (clone name: 201B2 or 201B7), and the cells were cultured (Sample Groups 2 through 7). A peptide free-group (comparative example) using cells cultured under the same conditions as in Sample groups 2 through 7 without the addition of a peptide was also established as a control group. A part of each culture liquid (culture supernatant) from the iPS cell cultures of each of the Sample Groups 2 through 7 and the peptide free group was collected on arbitrary days (8th, 11th, 13th, 15th, 18th and 20th day) after initiation of culture of iPS cells in the presence of the peptides.

The AFP contained in the collected culture supernatant was defected by dot blotting. Specifically, this was done as follows.

First, each collected culture supernatant was diluted 100 times with PBS. 2 µL, of each of the diluted culture supernatants was spotted (dripped) at intervals with no overlapping on a nitrocellulose membrane (GE Healthcare, Amersham® Protan Premium NC 0.2, Cat. No. 10600081). The nitrocellulose membrane with the spotted culture supernatants was then washed by shaking in PBS containing 0.1% Tween 20® (hereunder called "PBST"). The washed nitrocellulose membrane was then immersed in StartingBlock T20 (PBS) Blocking Buffer (Pierce Co.), and shaken overnight (about 16 to 24 hours) at 4° C. to perform blocking.

After being blocked, the nitrocellulose membrane was then washed by shaking it in PBST.

Next, in order to detect the AFP contained in the culture supernatant spotted on the nitrocellulose, an antigen-antibody reaction was performed using anti-AFP antibody (from rabbit, Dako Cytomation, Cat. No. A0008, Lot. No. 00052184) as a primary antibody and anti-rabbit IgG antibody labeled with HRP (horseradish peroxidase) (from goat, GE Healthcare, Cat. No. NA934V, Lot. No. 399405) as a secondary antibody. Specifically the primary antibody was diluted 5000 times with Can Get Signal® immunoreaction enhancer (Toyobo Co., Ltd.), and the nitrocellulose membrane was immersed in the diluted primary antibody solution and reacted for about one hour at room temperature (about 25° C.). After completion of the antigen-antibody reaction with the primary antibody, the nitrocellulose membrane was washed by shaking it in PBST. The washed nitrocellulose membrane was then immersed in a diluted solution of the secondary antibody diluted 10,000 times with Can Get Signal® immunoreaction enhancer (Toyobo Co., Ltd.), and reacted for about one hour at room temperature (about 25° C.).

After completion of the antigen-antibody reaction with the secondary antibody, Lumina Crescendo Western HRP Substrate (Merck Millipore Corp.) was dripped on the nitrocellulose membrane to react the substrate with the HRP-labeled antibody (secondary antibody), and the target protein (AFP) was detected with a LAS-3000 luminescent image analyzer (Fuji Film). Results are shown in FIG. 5.

Figure 5:
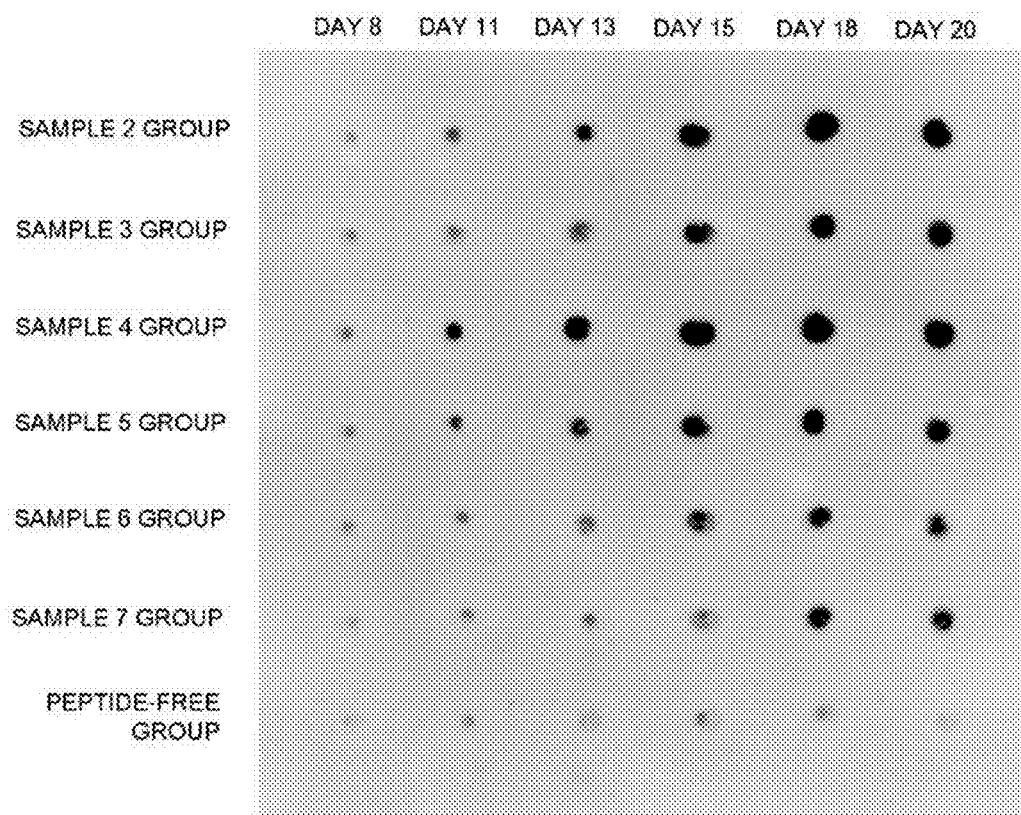
FIG. 5 is a photographic image showing the results of measurement of AFP levels in culture supernatant of iPS cells cultured after addition of differentiation-inducing synthetic peptides of one embodiment. The results for the Sample 2 through Sample 7 addition groups and Peptide-free group (Control) are shown in that order from the top, while the results for culture supernatant in each test group after 8, 11, 13, 15, 18 and 20 days of culture in the presence of the peptides are plotted from left to right.

As shown in FIG. 5, the amount of AFP in the culture supernatant collected from the peptide-free group did not change as the iPS cell culture time progressed. On the other hand, the amount of AFP in the culture supernatant collected from Sample Group 2 through Sample Group 7 increased dramatically as the culture time progressed in the presence of the peptide, in comparison with the amount of AFP in the culture supernatant collected from the peptide-free group with the same culture time. The increase in the AFP in the culture supernatant collected from the Sample 4 group was particularly dramatic. This confirms that iPS cells can be induced to differentiate into endodermal cells (typically liver precursor cells) by supplying the peptides of Samples 2 to 7 (especially Sample 4) to the iPS cells (typically, a culture liquid containing the cultured iPS cells).

These results show that the differentiation-inducing synthetic peptide disclosed here (and thus the stem cell differentiation inducer containing that peptide) has the stem cell differentiation-inducing activity to differentiate pluripotent stem cells in an undifferentiated state into endodermal cells. It also shows that the differentiation-inducing synthetic peptide disclosed here (and thus the stem cell differentiation inducer containing that peptide) has the stem cell differentiation-inducing activity to differentiate pluripotent stem cells in an undifferentiated state into liver precursor cells and hepatocytes (hepatocyte-like cells).

Although detailed data are not given here, in each test of evaluating the differentiation-inducing activity of differentiation-inducing synthetic peptide in use of iPS cells, as described above, it was confirmed that there was some deviation in the number of days of expression of each gene and protein due to differences between medium lots and the culture conditions of the iPS cells.

Example 6: Preparation of Granules 50 mg of the synthetic peptides (differentiation-inducing synthetic peptides) of Samples 1 to 7 above, 50 mg of crystallized cellulose and 400 mg of lactose were mixed together, and kneaded after addition of 1 mL of a mixed solution of ethanol and water. The kneaded product was granulated by ordinary methods to obtain granules (granular composition) having the differentiation-inducing synthetic peptide disclosed here as a principal ingredient.

INDUSTRIAL APPLICABILITY

As discussed above, because the differentiation-inducing synthetic peptide disclosed here has the stem cell differentiation-inducing ability to differentiate pluripotent stem cells into endodermal cells, it can be used favorably with the aim of inducing differentiation or promoting induction of differentiation of target pluripotent stem cells (especially iPS cells from humans). Thus, the stem cell differentiation-inducer disclosed here can be used favorably as a composition for regenerative medicine for example.

REFERENCE SIGNS LIST (Sequence Listing Free Text)
    SEQ ID NOS:1~34 Synthetic peptides
[Sequence Tables]

The invention claimed is:

1. A composition for inducing differentiation of pluripotent stem cells into hepatocytes and/or liver precursor cells, comprising:
a pharmaceutically acceptable carrier; and
a synthetic peptide comprising:
   a stem cell differentiation-inducing peptide sequence that induces differentiation of pluripotent stem cells into hepatocytes and/or liver precursor cells, and
   a transmembrane peptide sequence at the N end of or C end of the amino acid sequence of the stem cell differentiation-inducing peptide sequence,
wherein the total number of amino acid residues constituting the synthetic peptide is 100 or less amino acid residues,
the transmembrane peptide sequence is selected from the amino acid sequences represented by any of SEQ ID NOs: 7 to 15, and
the stem cell differentiation-inducing peptide sequence is selected from the amino acid sequences of i) through iv) below:

i) Amino acid sequence of SEQ ID NO:1 below:

(SEQ ID NO: 1)
MAATGTAAAAATGRLLLLLLVGLTAPALA, or
a partial amino acid sequence of SEQ ID NO:1 having sequentially at least 13 continuous amino acid residues from the #15 leucine residue to the #27 alanine residue counting from the N-terminal amino acid residue of this amino acid sequence, or
a modified amino acid sequence in which one, two or three amino acid residues are conservatively substituted in the amino acid sequence of SEQ ID NO:1 or the partial amino acid sequence thereof;

ii) Amino acid sequence of SEQ ID NO:2 below:

(SEQ ID NO: 2)
MAATGTAAAAATGKLLVLLLLGLTAPAAA, or
a partial amino acid sequence of SEQ ID NO:2 having sequentially at least 12 continuous amino acid residues from the #16 leucine residue to the #27 alanine residue counting from the N-terminal amino acid residue of this amino acid sequence, or
a modified amino acid sequence in which one, two or three amino acid residues are conservatively substituted in the amino acid sequence of SEQ ID NO:2 or the partial amino acid sequence thereof;

iii) Amino acid sequence of SEQ ID NO:3 below:

(SEQ ID NO: 3)
MGPASPAARGLSRRPGQPPLPLLLPLLLLLLRAQPAIG, or
a partial amino acid sequence of SEQ ID NO:3 having sequentially at least 13 continuous amino acid residues from the #19 proline residue to the #31 leucine residue counting from the N-terminal amino acid residue of this amino acid sequence, or
a partial amino acid sequence of SEQ ID NO:3 having sequentially at least 13 continuous amino acid residues from the #26 leucine residue to the #38 glycine residue counting from the N-terminal amino acid residue of this amino acid sequence, or
a modified amino acid sequence in which one, two or three amino acid residues are conservatively substituted in the amino acid sequence of SEQ ID NO:3 or the partial amino acid sequence thereof; or iv) Amino acid sequence of SEQ ID NO:4 below:

(SEQ ID NO: 4)
MGPTSPAARGQGRRWRPPLPLLLPLSLLLLRAQLAVG, or
a partial amino acid sequence of SEQ ID NO:4 having sequentially at least 13 continuous amino acid residues from the #18 proline residue to the #30 leucine residue counting from the N-terminal amino acid residue of this amino acid sequence, or
a partial amino acid sequence of SEQ ID NO:4 having sequentially at least 13 continuous amino acid residues from the #25 leucine residue to the #37 glycine residue counting from the N-terminal amino acid residue of this amino acid sequence, or
a modified amino acid sequence in which one, two or three amino acid residues are conservatively substituted in the amino acid sequence of SEQ ID NO:4 or the partial amino acid sequence thereof.

2. The composition according to claim 1, wherein the synthetic peptide has the following amino acid sequence as the transmembrane peptide sequence:

(SEQ ID NO: 7)
KKRTLRKNDRKKR.

3. The composition according to claim 1, wherein the total number of amino acid residues constituting the synthetic peptide is 60 or less amino acid residues.

4. The composition according to claim 1, wherein the synthetic peptide has any of the following amino acid sequences:

```
                                           (SEQ ID NO: 26)
LLLLLLLVGLTAPAGKKRTLRKNDRKKR (SEQ ID NO: 30)
AAAAATGRLLLLLLVGLTAPALAKKRTLRKNDRKKR (SEQ ID NO: 31)
RLLLLLLVGLTAPALAKKRTLRKNDRKKR (SEQ ID NO: 32)
MAATGTAAAAATGKLLVLLLLGLTAPAAAKKRTLRKNDRKKR (SEQ ID NO: 33)
MAATGTAAAAATGRLLLLLLVGLTAPALAKKRTLRKNDRKKR (SEQ ID NO: 34)
MGPASPAARGLSRRPGQPPLPLLLPLLLLLLRAQPAIGK

KRTLRKNDRKKR.
```

5. The composition according to claim 1, which increases expression, in the pluripotent stem cells, of Alpha-Fetoprotein or albumin protein, which are proteins known as markers of differentiation into liver precursor cells and hepatocytes, respectively.

6. A method for inducing differentiation of pluripotent stem cells into hepatocytes and/or liver precursor cells in vitro, the method comprising:
culturing target pluripotent stem cells; and
supplying, at least once, the composition according to claim 1 to the pluripotent stem cells in the culture.

7. The differentiation inducing method according to claim 6, wherein the pluripotent stem cells are iPS cells (induced pluripotent stem cells) derived from humans or mammals other than humans.

8. A method for producing in vitro a culture containing hepatocytes and/or liver precursor cells from a culture containing pluripotent stem cells, wherein the composition according to claim 1 is supplied at least once to the culture containing the pluripotent stem cells in a process of inducing differentiation of pluripotent stem cells into hepatocytes in the culture.

* * * * *